US012758407B2

(12) United States Patent
Harrison et al.

(10) Patent No.: US 12,758,407 B2
(45) Date of Patent: Oct. 13, 2026

(54) INTRAVASCULAR IMPLANT

(71) Applicant: INTACT VASCULAR, INC., Wayne, PA (US)

(72) Inventors: William J. Harrison, Wayne, PA (US); Daniel P. Alexander, Wayne, PA (US); Michael A. Longo, Wayne, PA (US); Payman Saffari, Irvine, CA (US); Chad J. Smith, Wayne, PA (US)

(73) Assignee: INTACT VASCULAR, INC., Wayne, PA (US)

( * ) Notice: Subject to any disclaimer, the term of this patent is extended or adjusted under 35 U.S.C. 154(b) by 1305 days.

(21) Appl. No.: 17/606,197

(22) PCT Filed: Apr. 22, 2020

(86) PCT No.: PCT/US2020/029351
§ 371 (c)(1),
(2) Date: Oct. 25, 2021

(87) PCT Pub. No.: WO2020/219567
PCT Pub. Date: Oct. 29, 2020

(65) Prior Publication Data

US 2022/0241098 A1 Aug. 4, 2022

Related U.S. Application Data

(60) Provisional application No. 62/901,193, filed on Sep. 16, 2019, provisional application No. 62/838,862, filed on Apr. 25, 2019.

(51) Int. Cl.
*A61F 2/90* (2013.01)
*A61F 2/915* (2013.01)

(52) U.S. Cl.
CPC ...... *A61F 2/90* (2013.01); *A61F 2002/91558* (2013.01); *A61F 2002/91583* (2013.01);
(Continued)

(58) Field of Classification Search
CPC ................ A61F 2/90; A61F 2220/0025; A61F 2250/0098; A61F 2/958; A61F 2/966;
(Continued)

(56) References Cited

U.S. PATENT DOCUMENTS 6,334,871 B1 1/2002 Dor
6,464,720 B2 * 10/2002 Boatman ................ A61F 2/915 623/1.34
(Continued)

OTHER PUBLICATIONS

International Search Report and Written Opinion Dated Aug. 26, 2020 for International Application No. PCT/US2020/029351 Filed Apr. 22, 2020.

*Primary Examiner* — Sarah W Aleman
*Assistant Examiner* — Rachel S Highland

(57) ABSTRACT

An intravascular implant can include a pair of inner rings comprising a distal inner ring and a proximal inner ring. A plurality of inner bridges can extend between opposing adjacent apices of the distal and proximal inner rings. Each of the plurality of inner bridges can form an eyelet. The implant can include a pair of outer rings comprising a distal outer ring and a proximal outer ring. The distal and proximal outer rings that can each be formed by a plurality of struts connected by apices formed in a zig-zag pattern. A plurality of outer bridge members can include a plurality of outer bridge members that extend between opposing adjacent apices of the distal outer ring and distal inner ring and outer bridge members that extend between opposing adjacent apices of the proximal outer ring and proximal inner ring.

20 Claims, 16 Drawing Sheets

(52) U.S. Cl.
CPC ................. *A61F 2220/0025* (2013.01); *A61F 2250/0098* (2013.01)

(58) Field of Classification Search
CPC ...... A61F 2002/826; A61F 2002/91575; A61F 2/915; A61F 2002/91558
See application file for complete search history.

(56) References Cited

U.S. PATENT DOCUMENTS

| | | | | |
|---|---|---|---|---|
| 6,896,697 | B1 * | 5/2005 | Yip | A61F 2/915 623/1.15 |
| 10,702,407 | B1 * | 7/2020 | Armer | A61F 2/958 |
| 2003/0125799 | A1 | 7/2003 | Limon | |
| 2009/0319023 | A1 * | 12/2009 | Hildebrand | A61F 2/07 623/1.13 |
| 2010/0010622 | A1 * | 1/2010 | Lowe | A61F 2/915 623/1.46 |
| 2011/0190872 | A1 | 8/2011 | Anukhin | |
| 2011/0301690 | A1 * | 12/2011 | Giasolli | A61F 2/844 623/1.15 |
| 2013/0144375 | A1 | 6/2013 | Giasolli | |
| 2013/0253633 | A1 | 9/2013 | Limon | |

* cited by examiner

INTRAVASCULAR IMPLANT

INCORPORATION BY REFERENCE

This application is the U.S. National Phase application under 35 U.S.C. § 371 of International Application No. PCT/US2020/029351 filed Apr. 22, 2020, which claims priority benefit of U.S. Provisional Patent Application No. 62/838,862, filed on Apr. 25, 2019; and U.S. Provisional Patent Application No. 62/901,193, filed on Sep. 16, 2019, each of which is incorporated herein by reference in its entirety for all purposes.

BACKGROUND

Field

The disclosure relates to devices and methods that can be used to create or maintain a passage, such as an intravascular implant. The intravascular implant can be catheter-based for insertion into a vascular system of a subject.

Description of the Related Art

There are a number of medical conditions and procedures in which an implant such as a stent is placed in the body to create or maintain a passage. There are a wide variety of stents used for different purposes, from expandable coronary, vascular and biliary implants, to plastic stents used to allow th4e flow of urine between kidney and bladder.

Stents are often placed in the vascular system after a medical procedure, such as balloon angioplasty. Balloon angioplasty is often used to treat atherosclerotic occlusive disease. Atherosclerotic occlusive disease is the primary cause of stroke, heart attack, limb loss, and death in the US and the industrialized world. Atherosclerotic plaque forms a hard layer along the wall of an artery and can be comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty, which may be followed with stent placement.

SUMMARY

In certain applications of balloon angioplasty, a balloon is inflated to a size that is consistent with the original diameter of the artery prior to developing occlusive disease. When the balloon is inflated, the plaque and/or arterial wall can tear. Cleavage planes can form within the plaque and/or arterial wall, permitting the plaque and/or arterial wall to expand in diameter with the expanding balloon. Some of the cleavage planes created by tearing of the plaque and/or arterial wall with balloon angioplasty can form a dissection. A dissection occurs when a portion of the plaque and/or arterial wall is lifted away from the artery, is not fully adherent to the artery and may be mobile or loose. The plaque and/or arterial wall tissue that has been disrupted by balloon angioplasty protrudes into the flow stream. If the plaque and/or arterial tissue lifts completely into the pathway of blood flow, it may impede flow or cause acute occlusion of the blood vessel. Portions of the vessel with more calcified lesions may remain constricted after balloon dilation. In such situations, it can be advantageous to use an implant according to several embodiments of the present disclosure that is capable of holding loose plaque against a blood vessel wall to treat dissections as well as capable of expanding portions of the vessel that remain constricted. In several embodiments of the disclosure herein, the implant can have a configuration that is suited for both functions. In several embodiments, the implant has a radial force that is relatively constant across a range of outer diameters so that the implant can be used in a wide variety of vessel sizes, exhibiting sufficient radial force to expand the dissections or constricted portions of such a vessel, while also minimizing injury to the vessel tissue.

In some embodiments, an intravascular implant comprises a pair of inner rings comprising a distal inner ring and a proximal inner ring. The distal and proximal inner rings can be formed by a plurality of struts connected by apices to form in a zig-zag pattern. A plurality of inner bridges can extend between opposing adjacent apices of the distal and proximal inner rings. Each of the plurality of inner bridges can form an eyelet. A pair of outer rings comprise a distal outer ring and a proximal outer ring. The distal and proximal outer rings can each be formed by a plurality of struts connected by apices form in a zig-zag pattern. A plurality of outer bridge members can include a plurality of outer bridge members that extend between opposing adjacent apices of the distal outer ring and distal inner ring and outer bridge members that extend between opposing adjacent apices of the proximal outer ring and proximal inner ring. The intravascular implant may consist essentially of these features.

In some embodiments, an intravascular implant comprises a pair of inner rings comprising a distal inner ring and a proximal inner ring. The distal and proximal inner rings can be formed by a plurality of struts connected by apices to form in a zig-zag pattern. A plurality of inner bridges can extend between every other opposing adjacent apices of the distal and proximal inner rings. The remaining opposing adjacent apices of the distal and proximal inner rings may be unconnected. Each of the plurality of inner bridges can form an eyelet. A pair of outer rings comprise a distal outer ring and a proximal outer ring. The distal and proximal outer rings can each be formed by a plurality of struts connected by apices form in a zig-zag pattern. A plurality of outer bridge members can include a plurality of outer bridge members that extend between opposing adjacent apices of the distal outer ring and distal inner ring and outer bridge members that extend between opposing adjacent apices of the proximal outer ring and proximal inner ring. The intravascular implant may consist essentially of these features.

The eyelet on each of the plurality of inner bridges may be circular. The plurality of outer bridges may connect every other opposing adjacent apices of the distal outer ring and distal inner ring. The remaining opposing adjacent apices of the distal outer ring and distal inner ring may be unconnected. The plurality of outer bridges may connect every other opposing adjacent apices of the proximal outer ring and proximal inner ring. The remaining opposing adjacent apices of the proximal outer ring and proximal inner ring may be unconnected. The plurality of inner bridges may be located longitudinally between the plurality of outer bridges. The plurality of outer bridges may be linear. The implant may comprise Nitinol. The implant may be made of Nitinol. The eyelet may include a radiopaque marker. The implant may be self-expandable. The implant may have less than 5 columns of cells. The implant may consist of three columns of cells. The pair of inner rings, the plurality of inner bridges, the pair of outer rings and the plurality of outer bridge members may form cells and wherein there may be between 1 and 5 columns of cells. The pair of inner rings, the plurality of inner bridges, the pair of outer rings and the plurality of outer bridge members may form cells, and wherein there may be only three columns of cells. The implant may have an unconstrained axial length between 8 mm to 12 mm.

The implant may exhibit a change of radial expansion or compression force of less than 0.3 N/mm over at least a 4 mm outer diameter expansion range. The implant may have an expanded diameter that is greater than 7 mm. The implant may have an expanded diameter range of at least 4 mm to 8 mm. The expanded diameter range the implant may exhibit a change in both the radial expansion and compression force of less than 0.35 Newton per length of the implant along the implant's longitudinal axis (N/mm). The expanded diameter range the implant may exhibit a change in both the radial expansion and compression force of between 0.35 and 0.1 Newton per length of the implant along the implant's longitudinal axis (N/mm). The expanded diameter range the implant may exhibit a change in both the radial expansion and compression force of less than 3.5 Newtons. The expanded diameter range the implant may exhibit a change in both the radial expansion and compression force of between 3.5 and 1 Newton.

The implant may exhibit an expansion force during an expanded diameter range of at least 4 mm to 8 mm of between 0.7 and 0.18 Newton per length of the implant along the implant's longitudinal axis (N/mm). The implant may exhibit an expansion force during an expanded diameter range of at least 4 mm to 8 mm of between 7 and 2 Newtons. The implant may exhibit a compression force during an expanded diameter range of at least 4 mm to 8 mm of between 0.4 and 1.25 Newtons per length of the implant along the implant's longitudinal axis (N/mm). The implant may exhibit a compression force during an expanded diameter range of at least 4 mm to 8 mm of between 4 Newtons and 13 Newtons.

The implant may form tubular body and wherein the tubular body may have a compression force curve being a measure of an amount of radial compression force required to compress the tubular body along a range of outer diameters, and may have an expansion force curve being a measure of an amount of radial expansion force exerted by the tubular body when the implant self-expands through the range of outer diameters. The range of outer diameters may include at least 4 mm to 8 mm. Within the range of outer diameters the compression force may be greater than the expansion force and a difference between the radial force of the compression force curve and the expansion force curve may be no more than 0.40 Newtons per length of the implant along the implant's longitudinal axis (N/mm) through the range of outer diameters. The difference between the radial force of the compression force curve and the expansion force curve may greater than 0.10 Newtons per length of the implant along the implant's longitudinal axis (N/mm) through the range of outer diameters. The implant may exhibit a change in radial expansion force in the range of outer diameters that is no more than 0.50 Newtons per length of the implant along the implant's longitudinal axis (N/mm) through the range of outer diameters. The implant may exhibit a change in radial expansion force in the range of outer diameters that is no more than 5.0 Newtons through the range of outer diameters. The implant may exhibit a change in radial expansion force in the range of outer diameters that is no more than 4.0 Newtons through the range of outer diameters. The implant may exhibit a change in radial expansion force greater than 1.0 Newtons through the range of outer diameters. The range of outer diameters of the implant may include at least 4 mm to 8 mm, and a maximum compression force of the implant may be less than 13 N and a minimum expansion force at 8 mm may be greater than 1.5 N and a change in radial compression force or expansion force in a treatment range may be less than 3.5 N. The maximum compression force of the implant may be between 9 and 13 N. The minimum expansion force at 8 mm may be between 1.5 N and 3.5 N. The change in radial compression force or expansion force in the treatment range may be between 3.5 N and 1 N.

In some embodiments, a self-expandable intravascular implant comprises a plurality of struts connected by apices in a zig-zag pattern to form a tubular body having a distal end and a proximal end and a lumen extending there through. The tubular body has an expansion force curve also referred to herein as chronic outward force (COF) being a measure of the amount of radial expansion force exerted by the tubular body when the tubular body self-expands through the range of outer diameters. In several embodiments, the range of outer diameters can include at least 4 mm to 8 mm, wherein the implant can exhibit a change in radial expansion force in the range of outer diameters that is no more than about 0.50 (N/mm) Newtons per length of the implant along the implant's longitudinal axis through the range of outer diameters. The intravascular implant may consist essentially of these features.

In some embodiments, a self-expandable intravascular implant comprises a plurality of struts connected by apices in a zig-zag pattern to form a tubular body having a distal end and a proximal end and a lumen extending there through. The tubular body has an expansion force curve also referred to herein as chronic outward force (COF) being a measure of the amount of radial expansion force exerted by the tubular body when the tubular body self-expands through the range of outer diameters. In several embodiments, the range of outer diameters can include at least 4 mm to 8 mm, wherein the implant can exhibit a change in radial expansion force in the range of outer diameters that is no more than about 0.40 (N/mm) Newtons per length of the implant along the implant's longitudinal axis through the range of outer diameters. The intravascular implant may consist essentially of these features.

The implant may exhibit the change in radial expansion force of no more than 0.40 Newtons per length of the implant along the implant's longitudinal axis (N/mm) through the range of outer diameters. The difference between the radial force of the compression force curve and the expansion force curve may be greater than about 0.10 Newtons per length of the implant along the implant's longitudinal axis (N/mm) through the range of outer diameters. The implant may have less than 5 columns of cells. The implant may consists of or consist essentially of three columns of cells. The intravascular implant may be self-expandable. The plurality of struts may form cells and wherein there may be between 1 and 5 columns of cells. The plurality of struts may form cells and wherein there may be only three columns of cells. The implant may have an unconstrained axial length between 8 mm to 12 mm.

In some embodiments, an intravascular implant comprises a plurality of struts connected by apices in a zig-zag pattern to form a tubular body having a distal end and a proximal end and a lumen extending there through. The tubular body can have an expansion force curve being a measure of an amount of radial expansion force exerted by the tubular body when the implant self-expands through the range of outer diameters. The range of outer diameters can include at least 4 mm to 8 mm. The implant can exhibit a change in radial expansion force in the range of outer diameters that is no more than about 0.50 Newtons per length of the implant along the implant's longitudinal axis (N/mm) through the range of outer diameters.

The implant may exhibit a change in radial expansion force in the range of outer diameters that is no more than 0.50 Newtons per length of the implant along the implant's longitudinal axis (N/mm) through the range of outer diameters. The implant may exhibit the change in radial expansion force of no more than about 0.40 Newtons per length of the implant along the implant's longitudinal axis (N/mm) through the range of outer diameters. The implant may exhibit the change in radial expansion force of no more than 0.40 Newtons per length of the implant along the implant's longitudinal axis (N/mm) through the range of outer diameters. .The implant may exhibit the change in radial expansion force greater than about 0.10 Newtons per length of the implant along the implant's longitudinal axis (N/mm) through the range of outer diameters. The implant may exhibit the change in radial expansion force greater than 0.10 Newtons per length of the implant along the implant's longitudinal axis (N/mm) through the range of outer diameters. The implant may have less than 5 columns of cells. The implant may consist of or consist essentially of three columns of cells. The plurality of struts may form cells and wherein there may be between 1 and 5 columns of cells. The plurality of struts may form cells and wherein there may be only three columns of cells. The implant may have an unconstrained axial length between 8 mm to 12 mm.

In some embodiments, an intravascular implant can comprise a plurality of struts connected by apices in a zig-zag pattern to form a tubular body having a distal end and a proximal end and a lumen extending there through. The tubular body can have an expansion force curve being a measure of an amount of radial expansion force exerted by the tubular body when the implant self-expands through the range of outer diameters. The range of outer diameters can include at least 4 mm to 8 mm. The implant can exhibit a change in radial expansion force in the range of outer diameters that is no more than about 5.0 Newtons through the range of outer diameters.

The implant can exhibit a change in radial expansion force in the range of outer diameters that is no more than 5.0 Newtons through the range of outer diameters. The implant may exhibit a change of radial expansion force of no more than about 4.0 Newtons through the range of outer diameters. .The implant may exhibit a change of radial expansion force of no more than 4.0 Newtons through the range of outer diameters. The implant may exhibit a change in radial expansion force greater than about 1.0 Newtons through the range of outer diameters. The implant may exhibit a change in radial expansion force greater than 1.0 Newtons through the range of outer diameters. The implant may have less than 5 columns of cells. With respect to the cell columns, the implant may consist of or consist essentially of three columns of cells (e.g., there are only 3 columns of cells, wherein the cells are formed by the struts). In some embodiments, there are between 1 to 8 columns of cells (e.g., 1-2, 3-4, 5-6, 8-10, and numerals that fall between those ranges) and between 3-15 rows of cells (e.g., 3-5, 5-7, 8-10, 10-15, and numerals that fall between those ranges). In some embodiments, the ratio of columns to rows is 1:1, 1:1.5, 1:2, 1:2.5, 1:3, 1:3.5, 1:4 or 1:5. The plurality of struts may form cells and wherein there may be between 1 and 5 columns of cells. The plurality of struts may form cells and wherein there may be only three columns of cells. The implant may have an unconstrained axial length between 8 mm to 12 mm.

In some embodiments, an intravascular implant comprises a pair of inner rings that can include a distal inner ring and a proximal inner ring. The distal and proximal inner rings can each be formed by a plurality of struts connected by apices to form a zig-zag pattern. The implant can include a plurality of inner bridges that extend between opposing adjacent apices of the distal and proximal inner rings. Each of the plurality of inner bridges can form an eyelet. The implant can include a pair of outer rings comprising a distal outer ring and a proximal outer ring. The distal and proximal outer rings can each be formed by a plurality of struts connected by apices to form a zig-zag pattern. The implant can include a plurality of outer bridge members. The plurality of outer bridge members can include outer bridge members that extend between opposing adjacent apices of the distal outer ring and distal inner ring and the plurality of outer bridge members including outer bridge members that extend between opposing adjacent apices of the proximal outer ring and proximal inner ring. The implant can have an expansion force curve being a measure of an amount of radial expansion force exerted by the implant when the implant self-expands through the range of outer diameters. The range of outer diameters can include at least 4 mm to 8 mm. The implant can exhibit a change in radial expansion force in the range of outer diameters that is no more than about 5 Newtons through the range of outer diameters. The intravascular implant may consist essentially of these features.

The implant can exhibit a change in radial expansion force in the range of outer diameters that is no more than 5 Newtons through the range of outer diameters. The implant may exhibit a change in radial expansion force of no more than about 4 Newtons through the range of outer diameters. The implant may exhibit a change in radial expansion force of no more than 4 Newtons through the range of outer diameters. The implant may exhibit a change in radial expansion force greater than about 1 Newtons through the range of outer diameters. The implant may exhibit a change in radial expansion force greater than 1 Newtons through the range of outer diameters. The implant may have less than 5 columns of cells. The implant may consist of or consist essentially of three columns of cells. The implant may have an unconstrained axial length between 8 mm to 12 mm. The pair of inner rings, the plurality of inner bridges, the pair of outer rings and the plurality of outer bridge members may form cells and wherein there may be between 1 and 5 columns of cells. The pair of inner rings, the plurality of inner bridges, the pair of outer rings and the plurality of outer bridge members may form cells, and wherein there may be only three columns of cells.

In some embodiments, an intravascular implant comprises a plurality of struts connected by apices in a zig-zag pattern to form a tubular body having a distal end and a proximal end and a lumen extending there through. The tubular body can have a compression force curve being a measure of an amount of radial compression force required to compress the tubular body along a range of outer diameters and can have an expansion force curve being a measure of an amount of radial expansion force exerted by the tubular body when the implant self-expands through the range of outer diameters. The range of outer diameters can include at least 4 mm to 8 mm. A maximum compression force of the implant is less than 13 N and a minimum expansion force at 8 mm is greater than 1.5 N and a change in radial compression force or expansion force in a treatment range is less than 3.5 N.

The intravascular implant may have a maximum compression force between 9 N to 13 N. The intravascular implant may have a minimum expansion force at 8 mm between 1.5 N and 3.5 N. The intravascular implant may exhibit a change in radial compression force or expansion force in the treatment range between 3.5 N and 1 N. The implant may have less than 5 columns of cells. The implant may consist of or consist essentially of three columns of cells. The implant may have an unconstrained axial length between 8 mm to 12 mm. The plurality of struts may form cells and wherein there may be between 1 and 5 columns of cells. The plurality of struts may form cells and wherein there may be only three columns of cells.

In some embodiments, a method of treating a blood vessel advancing a plurality of implants according to any one of the embodiments described above to a treatment area in a blood vessel after a balloon angioplasty has been performed at the treatment area. Each of the implants of the plurality of implants having a distal most end and a proximal most end along a longitudinal axis, and having an implant length defined by the distance between the distal most end and the proximal most end. A first implant of the plurality of implants is expanded against a wall of the blood vessel at the treatment area. A second implant of the plurality of implants is expanded against the wall of the blood vessel at the treatment area. The second implant spaced away from the first implant such that a portion of the treatment area between the first and second implants that has been treated by the balloon angioplasty includes diseased tissue that is not covered by the plurality of implants.

The method may include expanding a third implant and a fourth implant of the plurality of the implants against the wall of the blood vessel at the treatment area. The third implant may be spaced away from the fourth implant such that a portion of the treatment area between the third and fourth implants that has been treated by the balloon angioplasty includes diseased tissue that is not covered by the plurality of implants. The method may include treating a blood vessel wherein the treatment area includes a dissection. The method may include treating a blood vessel wherein the treatment area includes residual stenosis. The method may include treating a blood vessel wherein the treatment area is within a SFA or proximal popliteal arteries.

In some embodiments, a system for delivering a vascular prosthesis or implant according to any of the embodiments above can include a first elongate body comprising a proximal end, a distal end, and a plurality a vascular prosthesis or implant according to any of the embodiments disposed on the first elongate body. A sheath having a proximal end, a distal end. The sheath is moveable relative to the first elongate body from a first position in which the distal end of the sheath is disposed distally of a distal-most implant of the plurality of implant to a second position in which the distal end of the sheath is disposed proximally of the distal-most implant. Wherein the system is configured to place at least two implants of the plurality of implants at a treatment zone at spaced apart locations such that a minimum gap is provided in the treatment zone between a distal end of a proximal implant and a proximal end of a distal implant without requiring the plurality of delivery platforms be moved between deployment of the at least two implants.

In some embodiments, a system for delivering a vascular prosthesis according to any one of above embodiments comprises a first elongate body comprising a proximal end, a distal end, and a plurality of delivery platforms disposed adjacent to the distal end. A sheath having a proximal end, a distal end, and a second elongate body extends between the proximal end of the sheath and the distal end of the sheath. The sheath is moveable relative to the first elongate body from a first position in which the distal end of the sheath is disposed distally of a distal-most delivery platform of the plurality of delivery platforms to a second position in which the distal end of the sheath is disposed proximally of at least one delivery platform of the plurality of delivery platforms. A plurality of implants according to any one of embodiments wherein each implant of the plurality of implants is disposed about a corresponding delivery platform of the plurality of delivery platforms. The system is configured to place at least two implants of the plurality of implants at a treatment zone at spaced apart locations such that a minimum gap is provided in the treatment zone between a distal end of a proximal implant and a proximal end of a distal implant without requiring the plurality of delivery platforms be moved between deployment of the at least two implants.

In the system for delivering a vascular prosthesis, the system may include a plurality of implants wherein at least two implants are identical. They system may be configured such that each of the plurality of delivery platforms comprises a recess extending distally of a radial protrusion.

In some embodiments, the system for delivering a vascular prosthesis or implant may include at least two implants that are identical. The system for delivering a vascular prosthesis or implant may include a plurality of delivery platforms that can each comprise a recess extending distally of a radial protrusion. In some embodiments, a method of treating a blood vessel comprising an implant according to any one of the above embodiments to a treatment area in a blood vessel after a balloon angioplasty has been performed at the treatment area, expanding a first implant of the plurality of implants against a wall of the blood vessel at the treatment area; and expanding the implant against the wall of the blood vessel at the treatment area.

In some embodiments, a system for delivering a vascular prosthesis according to any of the above embodiments can include a first elongate body comprising a proximal end, a distal end, and at least one delivery platform disposed adjacent the distal end. A sheath having a proximal end, a distal end, and a second elongate body extending between the proximal end of the sheath and the distal end of the sheath, the sheath being moveable relative to the first elongate body from a first position in which the distal end of the sheath is disposed distally to at least one delivery platform to a second position in which the distal end of the sheath is disposed proximally of at least one delivery platform; and an implant according to any one of the above embodiments, the implant being disposed about the at least one delivery platform.

The system for delivering a vascular prosthesis may be configured such that the least delivery platform comprises a recess extending distally of a radial protrusion. The system may comprise a plurality of delivery platforms and each of the plurality of delivery platforms includes an implant according to any one of the above embodiments, the implant may be disposed about the at least one delivery platform. The system for delivering a vascular prosthesis may be configured such that each of the plurality of delivery platforms comprises a recess. The system for delivering a vascular prosthesis wherein each of the plurality of delivery platforms may comprise a recess extending distally of a radial protrusion.

In some embodiments, a system for delivering a vascular prosthesis comprising a first elongate body comprising a proximal end, a distal end, and plurality of implants according to any one of the above embodiments, the plurality of implants being disposed about the first elongate body; a sheath having a proximal end, a distal end, the sheath being moveable relative to the first elongate body from a first position in which the distal end of the sheath is disposed distally to at least one of the plurality of implants to a second position in which the distal end of the sheath is disposed proximally of at least one of the plurality of implants.

In some embodiments, a method of treating a blood vessel, the method comprises identifying a treatment area comprising residual stenosis as evidenced by a lack of luminal gain after balloon angioplasty; advancing a plurality of implants to the treatment area in a blood vessel after a balloon angioplasty has been performed at the treatment area, each of the implants of the plurality of implants having a distal most end and a proximal most end along a longitudinal axis, and having an implant length defined by the distance between the distal most end and the proximal most end; expanding a first implant of the plurality of implants against a wall of the blood vessel at the treatment area; and expanding a second implant of the plurality of implants against the wall of the blood vessel at the treatment area, the second implant spaced away from the first implant such that a portion of the treatment area between the first and second implants that has been treated by the balloon angioplasty includes diseased tissue that is not covered by the plurality of implants.

In some embodiments, an intravascular implant may be arranged as substantially as described herein or shown in the accompanying drawings. In some embodiments, a method of treating a blood vessel may be as herein described or shown in the accompanying drawings.

In some embodiments, an intravascular implant comprises a pair of inner rings comprising a distal inner ring and a proximal inner ring. The distal and proximal inner rings can be formed by a plurality of struts connected by apices to form in a zig-zag pattern. A plurality of inner bridges can extend between opposing adjacent apices of the distal and proximal inner rings. A pair of outer rings comprise a distal outer ring and a proximal outer ring. The distal and proximal outer rings can each be formed by a plurality of struts connected by apices form in a zig-zag pattern. A plurality of outer bridge members can include a plurality of outer bridge members that extend between opposing adjacent apices of the distal outer ring and distal inner ring and outer bridge members that extend between opposing adjacent apices of the proximal outer ring and proximal inner ring.

BRIEF DESCRIPTION OF THE DRAWINGS

Various embodiments are depicted in the accompanying drawings for illustrative purposes and should in no way be interpreted as limiting the scope of the inventions, in which like reference characters denote corresponding features consistently throughout similar embodiments.

DETAILED DESCRIPTION

Figure 1:
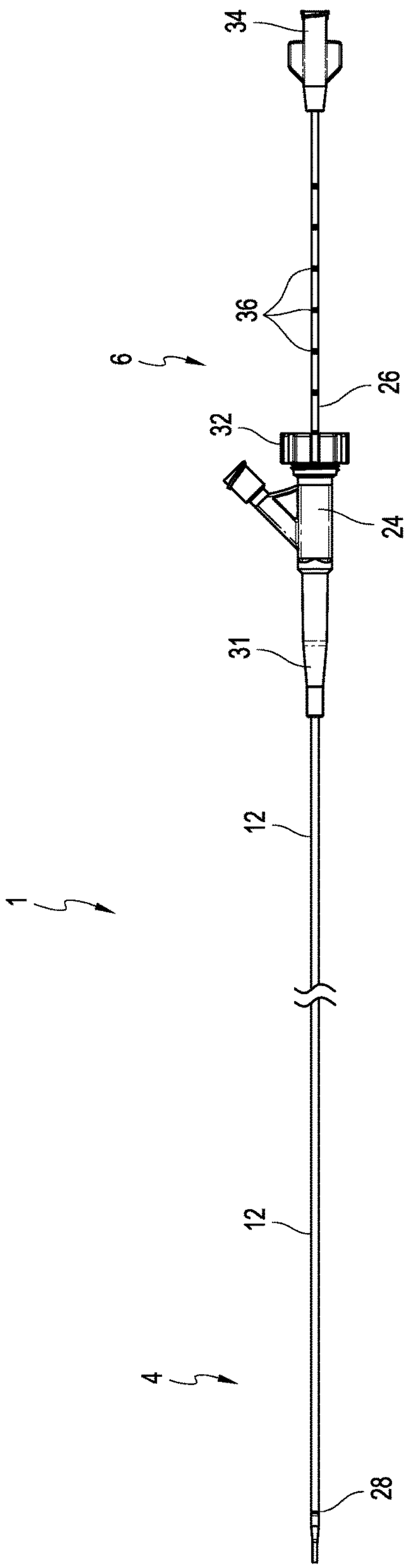
FIG. 1 is a side view of a delivery catheter that has been shortened to facilitate illustration.

The disclosure relates generally to devices and methods that can treat atherosclerotic occlusive disease. For example, aspects of this disclosure include an improved implant that can hold loose plaque and/or arterial tissue (dissections) against a blood vessel wall. The implant can advantageously be used to treat dissections or residual stenosis in non-calcified, moderately calcified or severely calcified lesions. Residual stenosis can be evidenced by a lack of luminal gain after balloon angioplasty as can be determined by fluoroscopy after injection of a contrast agent. The implants can be catheter based for insertion into a vascular system of a subject. In certain arrangements, the device is configured to treat calcified lesions and/or severely calcified lesions, which in several embodiments can be in the peripheral arteries, such as the superficial femoral artery (SFA) and proximal popliteal arteries. In several embodiments, the devices and methods described herein are used in vessels that have calcified lesions that have a grade of at least 3 on the Peripheral Arterial Calcium scoring system (PACSS). In some embodiments, the vessel being treated exhibits bilateral calcification that is less than 5 cm in length. In some embodiments, the vessel being treated exhibits bilateral calcification that is greater than 5 cm in length and/or greater than half the length of the lesion. In several embodiments, the calcification being treated is greater than 180 degrees around the circumference of the vessel, which as noted above can be peripheral arteries, such as the superficial femoral artery (SFA) and proximal popliteal arteries. In some embodiments, the vessel has at least 5 cm of unilateral or bilateral calcification. In several embodiments, a combination of scoring systems may be used to define the degree of calcification present within target lesions. In some embodiments, prior to treatment, a subject is identified as having one or more lesions, which may be calcified or severely calcified vessels by, for example, at least one of fluoroscopy, digital subtraction angiography, computed tomographic (CT) scan (e.g., using contrast (e.g., comprising iodine)), magnetic resonance imaging (MRI) (e.g., using contrast (e.g., comprising gadolinium)), duplex ultrasonography, pulse wave velocity measurement, echocardiography, radiograph (e.g., planar radiograph), measurement of the ankle-brachial index (ABI), etc. Factors such as age, presence of type-2 diabetes, and medical history (e.g., time on dialysis, incidence of stroke, incidence of myocardial infarction) may be indicative of calcification. Calcification may be medial calcification, intimal calcification, and/or a combination of medial calcification and intimal calcification. As noted above, the lesions described above as being treated and/or identified can be within the peripheral arteries such as the superficial femoral (SFA) and proximal popliteal arteries.

While useful, the embodiments described herein are often described in the context of holding loose plaque and/or arterial tissue (dissections) against a blood vessel wall, certain advantages and features of the embodiments disclosed herein can find utility in other applications such as, for example, medical applications in which it is desirable to create or preserve unobstructed blood flow in a blood vessel.

A. Delivery Catheter

A delivery catheter 1 can be used as part of a procedure to treat atherosclerotic occlusive disease. The delivery catheter can be used to deliver one or more implants 2 which can also be referred to herein as an intravascular implant, such as a stent, to a site of plaque accumulation. The intravascular implant(s) 2 can stabilize the site and/or hold pieces of plaque out of the way of blood flow. The delivery catheter 1 is described with respect to implants 2 shown partially in FIGS. 1-3A. Additional, views details and embodiments of the implants labeled with reference number 2 in FIGS. 1-3A that can be used with the delivery catheter 1 will be explained in detail below with reference to reference number 10 in FIGS. 4A-D. In certain embodiments, the delivery catheter 1 can be used to deliver implants, such as embodiments of the implants 10 described in detail with reference to FIGS. 4A-4D. Embodiments of the implants 10 described with reference to FIGS. 4A-4D can advantageously have sufficient radial force to treat residual stenosis in non-calcified or calcified lesions and in several embodiments sufficient radial force to treat residual stenosis in non-calcified or calcified lesions in peripheral arteries such as the SFA and proximal popliteal arteries. It will be understood that although the implants and methods described herein are described primarily with reference to vascular procedures, certain features and aspects of the embodiments disclosed herein can also find utility used in treatments for other parts of the body.

Figure 2:
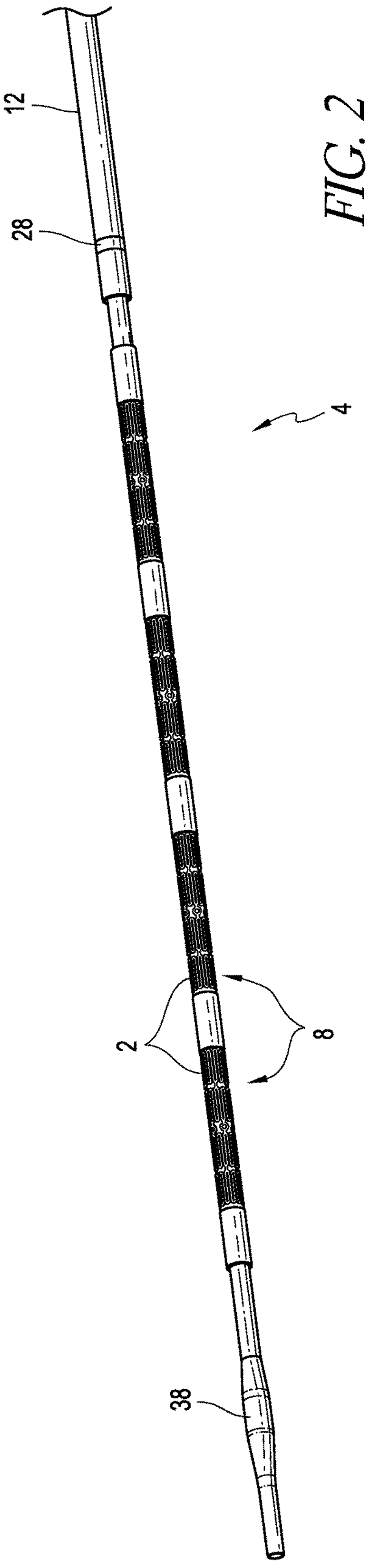
FIG. 2 shows a view of the distal end of the delivery catheter of FIG. 1 with the outer sheath withdrawn.

FIGS. 1 and 2 illustrate an embodiment of the delivery catheter 1 that can be used for sequential delivery of multiple implants 2, 10. The delivery catheter 1 can be used in procedures to treat atherosclerotic occlusive disease, though it is not limited to these procedures.

The delivery catheter 1 of FIG. 1, which has been shortened to facilitate illustration, highlights the distal 4 and proximal ends 6. The proximal end 6 can be held by a physician or other medical professional during a medical procedure. The proximal end 6 can be configured in a variety of manners such as, for example, a pin and pull configuration (as illustrated) or can be provided with an integrated handle assembly. The proximal end 6 can be used to control delivery of one or more implants 2. FIG. 2 shows the distal end 4 with four (4) implants 2, each positioned at a dedicated delivery platform 8. While FIGS. 1 and 2 illustrate a delivery catheter 1 with four (4) implants and four (4) dedicated delivery platforms, the delivery catheter can include more or less implants and delivery platforms such as 1, 2, 3, 5, 6, 7 or 8 implants and delivery platforms.

Comparing FIGS. 1 and 2, it can be seen that an outer sheath 12 has been withdrawn from the distal end in FIG. 2. This reveals the delivery platforms 8 and the respective implants 2. The implants 2 can be self-expandable and are shown in their compressed position to represent how they would fit in the delivery platforms. In use, the outer sheath 12 can cover the implants 2 when in this position. As will be discussed in more detail below, the outer sheath 12 can be withdrawn in a systematic manner to deploy one implant 2 at a time at a desired treatment location. Advantageously, the delivery catheter 1 can be used to implant relatively small implants that can be delivered at precise treatment locations and spaced appropriately to not overlap. It will be understood, that the delivery catheter and methods can also be used for other intraluminal devices, including larger devices, and are not limited to use with intraluminal devices described herein.

Returning now to FIG. 1, the proximal end 6 of the illustrated embodiment will now be described. The delivery catheter 1 can include the outer sheath 12, a proximal housing 24, and an inner shaft 26. The outer sheath 12 can be constructed as a laminate of polymer extrusions and braided wires embedded in the polymer extrusions. Flexibility and stiffness can be controlled through the number of braid wires, the braid pattern and pitch of the braid. In other embodiments, the outer sheath can be formed of a hypotube, such as a metal or plastic hypotube. Flexibility and stiffness of the sheath can be controlled by many features such as the slope and frequency of a spiral cut along the length of the hypotube. The outer sheath 12 may also include a radiopaque (RO) marker 28 at or near the distal end. In some embodiments, the radiopaque marker 28 can be an annular band spaced from the distal-most end.

As shown, the outer sheath 12 can comprise a braided shaft and the proximal housing 24 can include a bifurcation luer that connects to the outer sheath through a strain relief 31. The strain relief 31 can take a variety of forms, such as being made of polyolefin or other similar material.

The bifurcation luer 24 can include a main arm to receive the inner shaft 26 and a side arm. The bifurcation luer can be disposed at the proximal end of the outer sheath 12. The side arm can include a flushing port that can be used to inject heparinized saline to flush out air and increase lubricity in the space between the sheath 12 and the inner shaft 16.

A tuohy borst adapter, hemostatic valve, or other sealing arrangement 32 can be provided proximal of or integrated into the bifurcation luer 24 to receive and seal the proximal end of the space between the inner shaft 26 and the outer sheath 12. The tuohy borst adapter can also provide a locking interface, such as a screw lock, to secure the relationship between the outer sheath and the inner shaft. This can allow the physician to properly place the distal end without prematurely deploying an implant.

The inner shaft is shown with a proximal luer hub 34 and deployment reference marks 36. The deployment reference marks 36 can correspond with the delivery platforms 8, such that the spacing between each deployment reference mark can be the same as the spacing between features of the delivery platforms. For example, the space between deployment reference marks can be the same as the distance between the centers of the delivery platforms.

In some embodiments, a distal most deployment reference mark, or a mark that is different from the others, such as having a wider band or different color, can indicate a primary or home position. For example, a deployment reference mark with a wider band than the others can be aligned with the proximal end of the bifurcation luer 24 or hemostatic valve 32. This can indicate to a physician that the outer sheath 12 is in a position completely covering the inner shaft 26 proximal of a distal tip 38. In some embodiments, this alignment can also translate to alignment of the RO marker 28 on the outer sheath to a RO marker on the distal end of the inner shaft 26.

In some embodiments, one or more of the deployment reference marks 36 can represent the number of intravascular implants that are within the system. Thus, once an implant is released, the deployment reference mark 36 will be covered up and the physician can know that the remaining deployment reference marks correspond with the remaining number of implants available for use. In such an embodiment, the proximal end of the bifurcation luer 24 or hemostatic valve 32 can be advanced to be centered approximately between two reference marks to indicate deployment.

Figure 3:
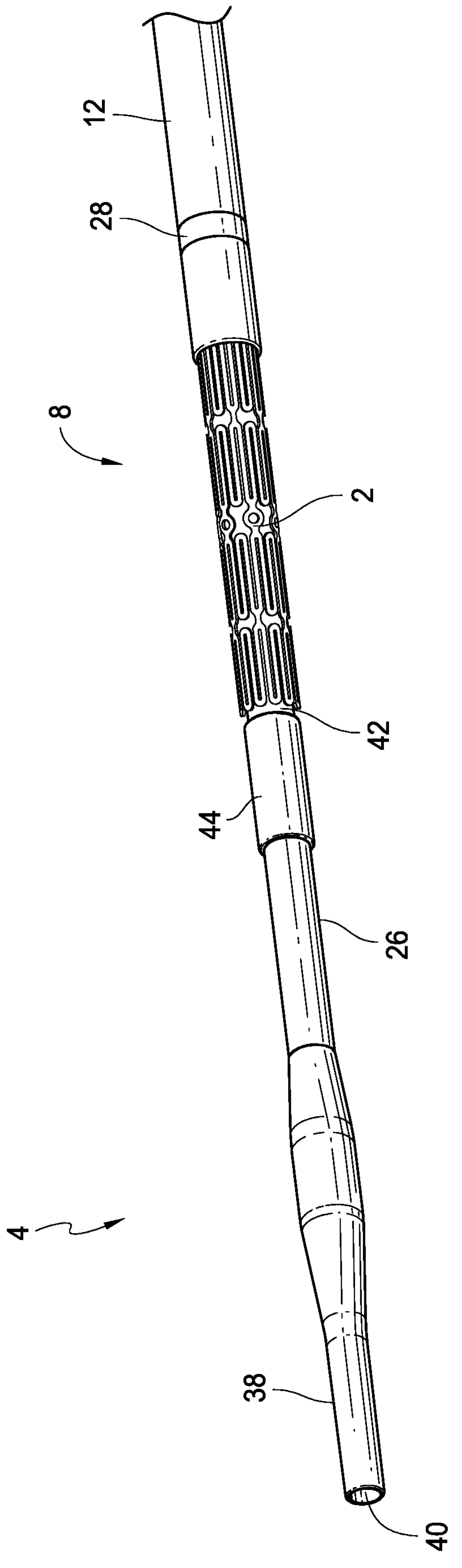
FIG. 3 illustrates a detail view of the distal end of the delivery catheter of FIG. 1 with the outer sheath partially withdrawn.

Turning now to FIG. 3, a detail view of the distal end 4 of the delivery catheter 1 is shown including the distal tip 38. The tip 38 can be a tapered nose cone and can be made of a soft material. The tip 38 serves as a dilating structure to atraumatically displace tissue and help to guide the delivery catheter 1 through the vasculature. The tip 38 itself may be radiopaque, or a radiopaque element (not shown) can be incorporated into or near the tip. A guidewire lumen 40 can be seen that can extend through the inner shaft 26 to the proximal luer hub 34 (FIG. 1). The guidewire lumen 40 can be configured for receipt and advancement of a guidewire therein.

Parts of one of the delivery platforms 8 are also shown. The delivery platforms 8 can be identical or substantially identical, though other embodiments can have delivery platforms of different sizes and constructions between different delivery platforms. A crimped or compressed implant 2 is shown in the delivery platform 8. In a similar manner, the implants positioned on the delivery platforms can be identical or substantially identical, though in other embodiments the implants can be different sizes and constructions.

Figure 3A:
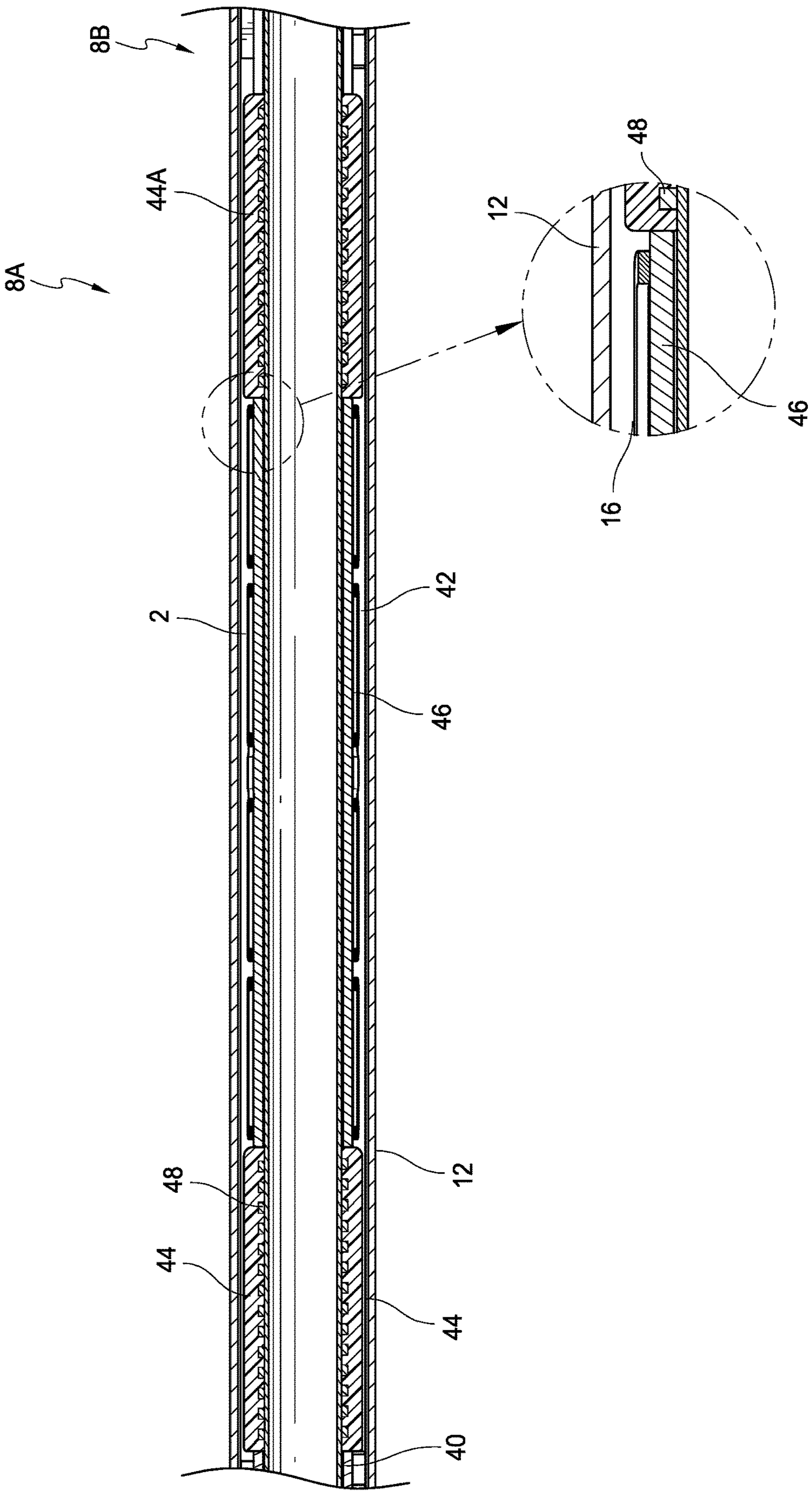
FIG. 3A is a cross-sectional view of a portion of the delivery catheter of FIG. 1 showing an embodiment of a delivery platform.

As can be seen in FIGS. 2 and 3, the one or more delivery platforms 8 can be disposed on the inner shaft 26 adjacent the distal end 4 of the delivery catheter 1. Each of the delivery platforms 8 can comprise a recess 42 positioned between a pair of annular pusher bands 44. FIG. 3A shows a cross section of the delivery catheter 1 at one embodiment of a delivery platform 8A. In the illustrated embodiment, the proximal annular pusher band 44A of a first platform 8A is also the distal annular pusher band 44A of the platform 8B located immediately proximal (only partially shown). The annular pusher band 44 has a larger outer diameter as compared to the delivery platform at the recess 42. In some embodiments, the recess can be defined as the smaller diameter region next to, or between, one or two annular pusher bands and/or an additional feature on the inner shaft 26. In a modified arrangement of the delivery catheter, the recesses could be eliminated by providing another structure for axially fixing the implant along the inner shaft 26 such as for example a peg or interlock that engages the implant 2.

One or more of the annular pusher bands 44 can be radiopaque marker bands. For example, proximal and distal radiopaque marker bands 44 can be provided to make the ends of the platform 8 visible using standard angiographic visualization techniques and thus indicate to the user the location of the implants on the delivery catheter. The annular marker bands 44 can take any suitable form, for example including one more of tantalum, iridium, and platinum materials. In embodiments that can be used with the implants 10 described below with respect to FIGS. 4A-5, the pusher bands 44 can be about 4 mm long with about 12 mm recesses between them. In such embodiments, an implant having an axial length of between 8-12 mm in one embodiment or 10-11 mm in another embodiment and 10.3 mm in another embodiment can be positioned between the pusher bands 44. In some embodiments, the pusher bands can be between 50-70% of the size of the recess and/or the implant. In some embodiments, the pusher bands are about 60%. In other embodiments, the pusher bands can be much smaller, at between 10-20% of the size of the recess and/or the implant. This may be the case especially with longer implants. In some embodiments, at least the proximal ends of the pusher bands 44 can have a radius to help reduce potential for catching on deployed implants during retraction of the delivery catheter.

Reducing the difference in length between the recess and the implant can increase the precision of placement of the implant, especially with implants having only one, two, three, or four columns of cells. As will be described in more detail below, a column of cells can be defined as a pair or rings and each ring can be formed by series of struts and apexes that can form a repeating pattern in certain embodiments. In such embodiments, implants with one, two, three, or four columns of cells can be formed by two, three, four or five rings respectively. As in some embodiments, the recess can be less than 1, 0.5, 0.4, 0.3, 0.25, or 0.2 mm longer than the implant. As noted above, the implant can be any number of different sizes, such as 4, 5, 6, 6.5, 8, 10, or 12 mm in axial length.

The outer sheath 12 can be made of polyether block amide (PEBA), a thermoplastic elastomer (TPE) available under the trade name PEBAX. As noted above, the outer sheath 12 can be constructed as a laminate of polymer extrusions and braided wires embedded in the polymer extrusions. Flexibility and stiffness can be controlled through the number of braid wires, the braid pattern and pitch of the braid. In some embodiments, the outer sheath 12 can have a thinner inner liner made of a polytetrafluoroethylene (PTFE) such as TEFLON. Any radiopaque marker band(s) 28 or other radiopaque material may be positioned between these two layers. In other embodiments, the radiopaque marker band(s) 28, or other radiopaque material can be embedded within one or more layers of the outer sheath 12. The radiopaque marker band(s) 28 can range from 0.5 mm to 5 mm wide and be located from 0.5 mm to 10 mm proximal from the distal-most tip 52. In some embodiments, the radiopaque marker band(s) 28 can be 1 mm wide and 6 mm proximal from the distal-most end of the sheath 12.

In the cross section of FIG. 3A it can be seen that a sleeve 46 can be positioned around the inner shaft 26 between the two annular bands 44. In some embodiments, the delivery platform 8 can comprise a sleeve 46 surrounding a shaft 26, where the sleeve 46 is made of a different material or has different material properties than the shaft 26. In some embodiments, the sleeve provides a material having a low durometer, a grip, a tread pattern, and/or other features to help the implants stay in place in the delivery platform. In some embodiments, the sleeve can be made of PEBA. The inner shaft according to some embodiments is a composite extrusion made of a PTFE/polyimide composite. The sleeve can be softer than (that is, a lower durometer than) the inner shaft and/or the pusher bands 44. This may be the case even if made of similar types of materials. In some embodiments, the sleeve 46 can be a material having a low durometer, a grip, a tread pattern, and/or other features to help the implant stay in place (e.g., longitudinal position with respect to the inner shaft) while the outer sleeve 12 is withdrawn. This can increase the amount of control during deployment and reduce the likelihood that the implant will shoot out distally from the delivery platform (known in the industry as watermelon seeding). In some cases the outer sheath 12 can be partially retracted thereby partially exposing an intraluminal device whereby the intraluminal device can partially expand while being securely retained by the delivery platform prior to full release.

The sleeve 46 can be sized so that with the implant 2 in the delivery platform 8 there is minimal to no space between the implant and the outer sheath. In some embodiments, the sleeve 46 can be co-molded with or extruded onto the inner shaft 26. In some embodiments, the delivery catheter 1 can be formed with a single sleeve 46 extending over a length of the inner shaft 26. For example, the sleeve can extend from the first delivery platform to the last delivery platform. The annular bands 44 may surround distinct sections of sleeve 46, or they may be encased by the sleeve 46. In some embodiments, each delivery platform 8 has a separate sleeve 46 positioned in the recess 42. The annular bands 44 may be encased by a different material, or may not be encased at all.

Figure 3B:
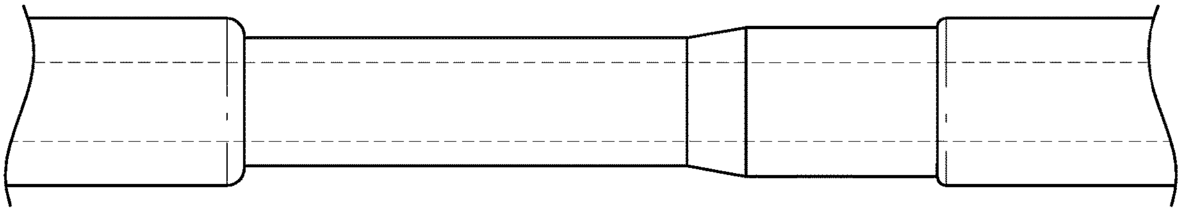
FIG. 3B is a side view of an embodiment of a delivery platform.

The sleeve 46 can be cylindrical with a circular cross-section that is maintained across a portion of or the entire length of the sleeve. FIG. 3B illustrates an embodiment wherein the sleeve 46 can have two different constant outer diameter sections with a short taper between them. The sleeve can be formed from two separate sections that are thermally bonded together. The tapered portion can also be created by thermal bonding so that there is a smooth transition between the two constant outer diameter sections. The larger constant outer diameter section can extend from the proximal end of the recess distally. This larger outer diameter section that may or may not have a constant outer diameter can extend along less than the entire recess. As shown in FIG. 3B, the sleeve 56 can have a unique shape and may include one or more of the following: tapering, an hourglass shape, ridges, dimples, dots, two or more different diameters, etc. Features such as ridges, dots, and dimples can be positioned in a number of different patterns or groupings. In addition, the sleeve, or a section of the sleeve can extend along less than the entire recess. In some embodiments, the length of the sleeve or larger outer diameter section can correspond to the length of the implant. For example, the sleeve or larger diameter section can extend ¾, ⅔, ½, ⅖, ⅓, or ¼ of the recess and/or implant. Further, the length of the sleeve or larger outer diameter section can be related to the size of struts in the implant, such as the struts in a proximal most undulating ring. For example, it can extend along the entire, ⅘, ¾, ⅔, or ½ of the length of a strut or the length of the proximal most undulating ring. A short sleeve, or a larger outer diameter section of a sleeve, preferably extends from the proximal end of the recess distally, but can also be centered in the recess, positioned on at the distal end, or at other positions within the recess In some embodiments, the inner shaft 26 can have the lower durometer sleeve 46 between pushers 44 as described above and the implant 2 can be crimped onto the sleeve 46 and an outer sheath 12 to constrain the crimped implant in place. The clearance between the sleeve 46 and the outer sheath 12 can result in a slight interference fit between the crimped implant 2 and the inner and outer elements. This slight interference can allow the delivery system 1 to constrain the crimped implant during deployment until it is almost completely unsheathed allowing the distal portion of the implant to “flower petal” open and engage the vessel wall, reducing the potential for jumping. In a modified embodiment, the pushers 44 can include indentations and/or protrusions that can engage portions of the implant 2 so as to lock the implant 2 to the catheter until outer sheath 12 is withdrawn past the indentations and/or protrusions on the pusher 44 to unlock the implant 2 from the catheter.

According to some embodiments, the inner shaft 26 can be made of a polyimide-PEBAX combination and the lower durometer PEBAX sleeve 46 can be thermally bonded in between pushers 44. The intravascular implant 2 can be crimped onto the sleeve 46 and a PTFE lined outer sheath 12 can constrain the crimped implant in place.

Returning to FIG. 3A, a feature of certain embodiments of the radiopaque marker band 44 is shown. As has been mentioned, the sleeve 46 may encase the annular bands 44. Alternatively, another material can encase the metallic bands to form the annular marker bands 44. The annular marker bands 44 can be made of wire 48 or multiple pieces of material or having slits to increase flexibility while remaining radiopacity. In some embodiments the wire can form a helical coil that is wrapped around the inner shaft 26.

It should be appreciated that while the delivery catheter 1 has certain features and advantages useful in combination with embodiments of the implant 2, 10 described herein, embodiments of the implant 2, 10 described above and below can be delivered with other types of delivery systems and catheters.

B. Implant Design

FIGS. 4A-4D illustrate an embodiment of the implant 10 (also referred to herein as an intravascular implant) having certain aspects and features according to the present disclosure. Advantageously, the implant 10 can be configured to treat dissections and, in particular, dissections where there is residual stenosis in, for example, more calcified lesions or highly calcified regions. As noted above, in several embodiments, the implant 10 can be configured to treat residual stenosis in calcified, severely calcified or non-calcified lesions in, for example, the peripheral arteries such as the SFA and proximal popliteal arteries.

The implant 10 can be catheter based for insertion into a vascular system of a subject and, in particular, as noted above, one or more of the implants 10 can be delivered using embodiments of the delivery catheter 1 described above. As will be described below, the intravascular implant 10 can include one or more circumferential members that have undulating, e.g., sinusoidal, configurations and that are spaced apart in the axial direction. The circumferential members can be coupled together at one or more circumferentially spaced locations by axially extending members, sometimes referred to herein as bridge members. Advantageously, in certain embodiments, the implants can be expandable over a wide range of diameters with certain advantageous force characteristics and, as discussed below, can be deployed in a variety of different vessels.

The implant 10 may be laser cut or etched out of a metal tube form. The implant can be made of a material such as a corrosion-resistant metal, polymer, composite or other durable, flexible material. A preferred material is a metal having “shape memory” (such as Nitinol). The implant 10 can be self-expanding. In an embodiment, the implant 10 is formed from a tube having wall thickness of about 0.15 mm to form a final implant having wall thickness of about 0.125 mm. In an embodiment, the wall thickness of the tube is uniform and in certain embodiments struts and loops and bridges that form the implant 10 have a thickness corresponding to the wall thickness of the tube from which the implant 10 is formed. In an embodiment, the wall thickness of the implant the struts and loops and bridges that form the implant 10 is uniform.

Figure 4A:
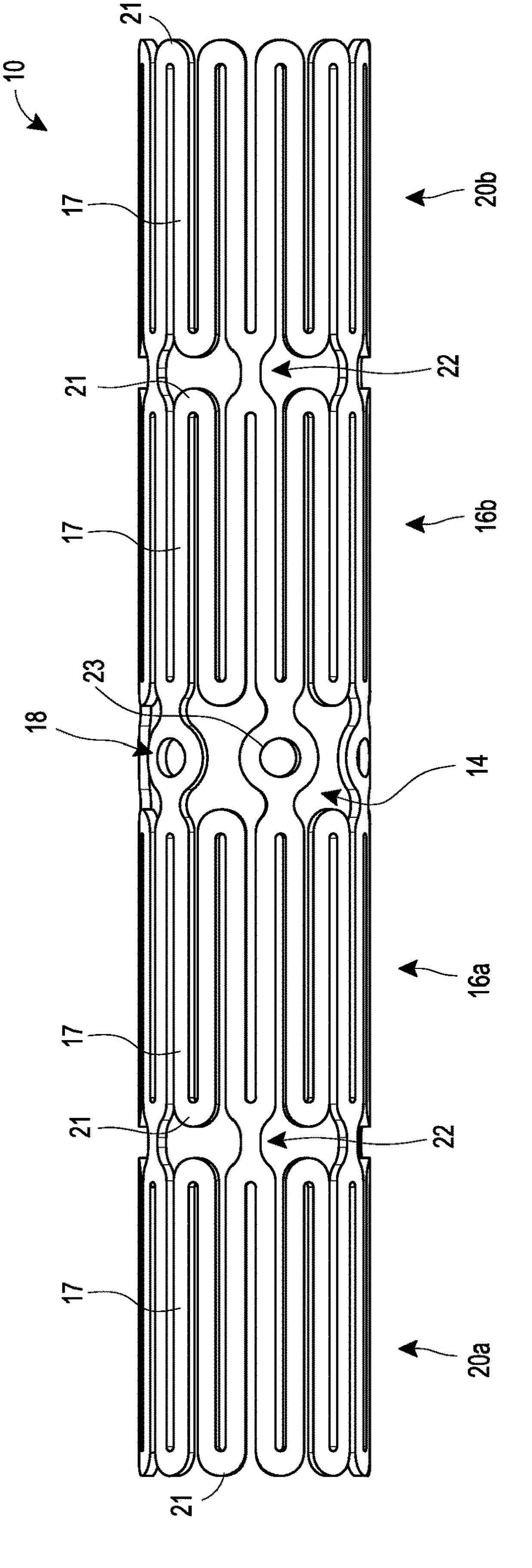
FIGS. 4A and 4B illustrate an embodiment of an intravascular implant according to aspects of the present disclosure in a collapsed state and in an expanded state, respectively.
Figure 4B:
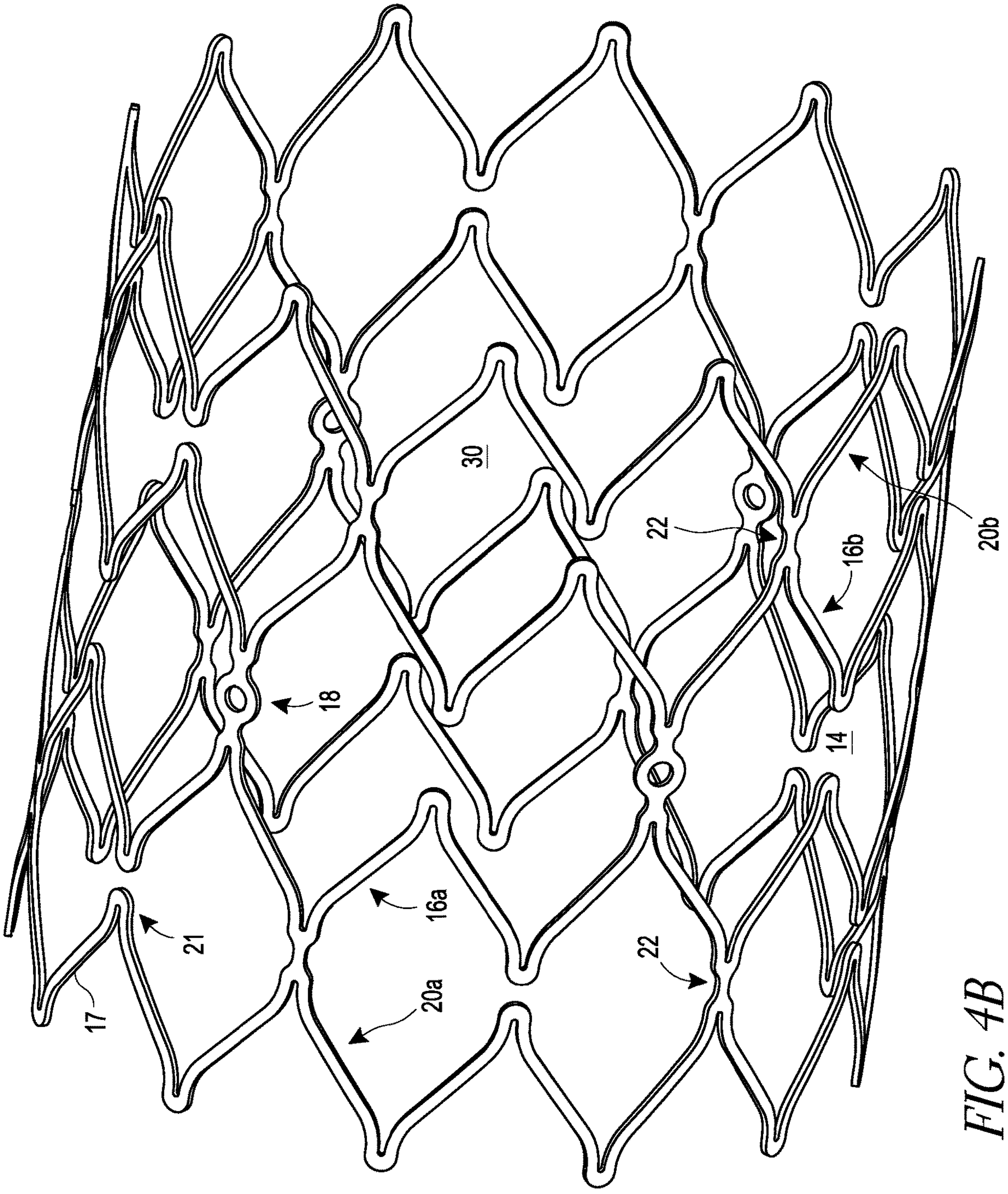

FIGS. 4A-B show the overall structure of the implant 10 according to an illustrated embodiment. FIG. 4A shows the implant 10 in a collapsed state while FIG. 4B shows the implant 10 in an expanded state The implant 10 can include a pair of inner circumferential rings 16*a,* 16*b* which can be formed by a plurality of struts 17 connected by loops 21 (also referred to herein as "apexes") to form in a zig-zag pattern in which the implant 10 forms a tubular body having a distal end and a proximal end with a lumen extending between the proximal and distal ends. The inner rings 16*a,* 16*b* can be referred to as the first and second rings 16*a,* 16*b* of the implant 10 or the distal inner ring 16*a* and proximal inner ring 16*b* of the implant 10. The inner circumferential rings 16*a,* 16*b* can be joined by inner bridges 18 that extend between the inner rings 16*a,* 16*b*. The inner rings 16*a*, 16*b* and inner bridges 18 can define a central column of bounded inner cells 14 along an outer surface of the implant 10 in which the boundary of each of the central cells 14 is defined by the inner bridges 18, loops 21 and struts 17. As shown, the two inner rings 16*a*, 16*b* can be mirror images of each other although in modified arrangements the two inner rings can have different configurations. The inner bridges 18 can be symmetrical across a transverse plane extending through the axial mid-point of the inner bridge 18, though other configurations are also possible. The inner rings 16*a,* 16*b,* can be considered coaxial, where that term is defined broadly to include two spaced apart rings, or structures, having centers of rotation or mass that are disposed along a common axis, e.g., the central longitudinal axis of the implant 10.

The inner bridges 18 can form an eyelet 23, which can be circular as shown in the illustrated embodiment. In an embodiment, the eyelet has a diameter of 0.3 mm. In other arrangements, the eyelet 23 can have other shapes and sizes such as oval, rectangular or square. As shown in FIGS. 4E and 4F, a marker 23A (not illustrated in FIGS. 4A-4D but shown in FIGS. 4E and 4F) can be positioned within the eyelet 23. The marker 23A can be fluoroscopically opaque or radiopaque. As shown in FIGS. 4E and 4F, each eyelet 23 can be provided with a marker 23A such that the implant 10 can be provided with a series of markers 23A which can each be radiopaque. In some embodiments, the eyelets 23 and thus also the markers 23A are at the longitudinal midline of the device. The markers 23A can be disposed between the two inner rings 16*a,* 16*b*. The radiopaque makers 23A can be formed a variety of materials such as gold, platinum or tantalum or combinations thereof.

As noted above, the radiopaque markers 23A can have one of many different shapes or configurations. In some embodiments, the radiopaque markers 23A have a planar or flat structure. The radiopaque markers 23A can be coupled to the implant 10 by being press-fit or riveted into, the eyelet 23 producing a flat leveled surface with the eyelet 23. The markers 23A can offer clear visibility of the implant 10 in the delivery catheter 1 and can provide guidance to the clinician for accurate placement during the procedure. According to certain delivery methods, due to the co-placement of the markers 23A at the inner bridges 18 at or near the longitudinal center of the implant 10, the markers 23A can offer a visible clue to the clinician of the point when the release of the implant 10 will take place. For example, once the markers 23A meet a marker strip located at the tip of a delivery catheter sheath the full device can be deployed. In a modified embodiment, a marker can be provided at other locations of the implant 10. For example, a marker can be positioned in an eyelet extending from a proximal and/or distal end of the implant.

Figure 4C:
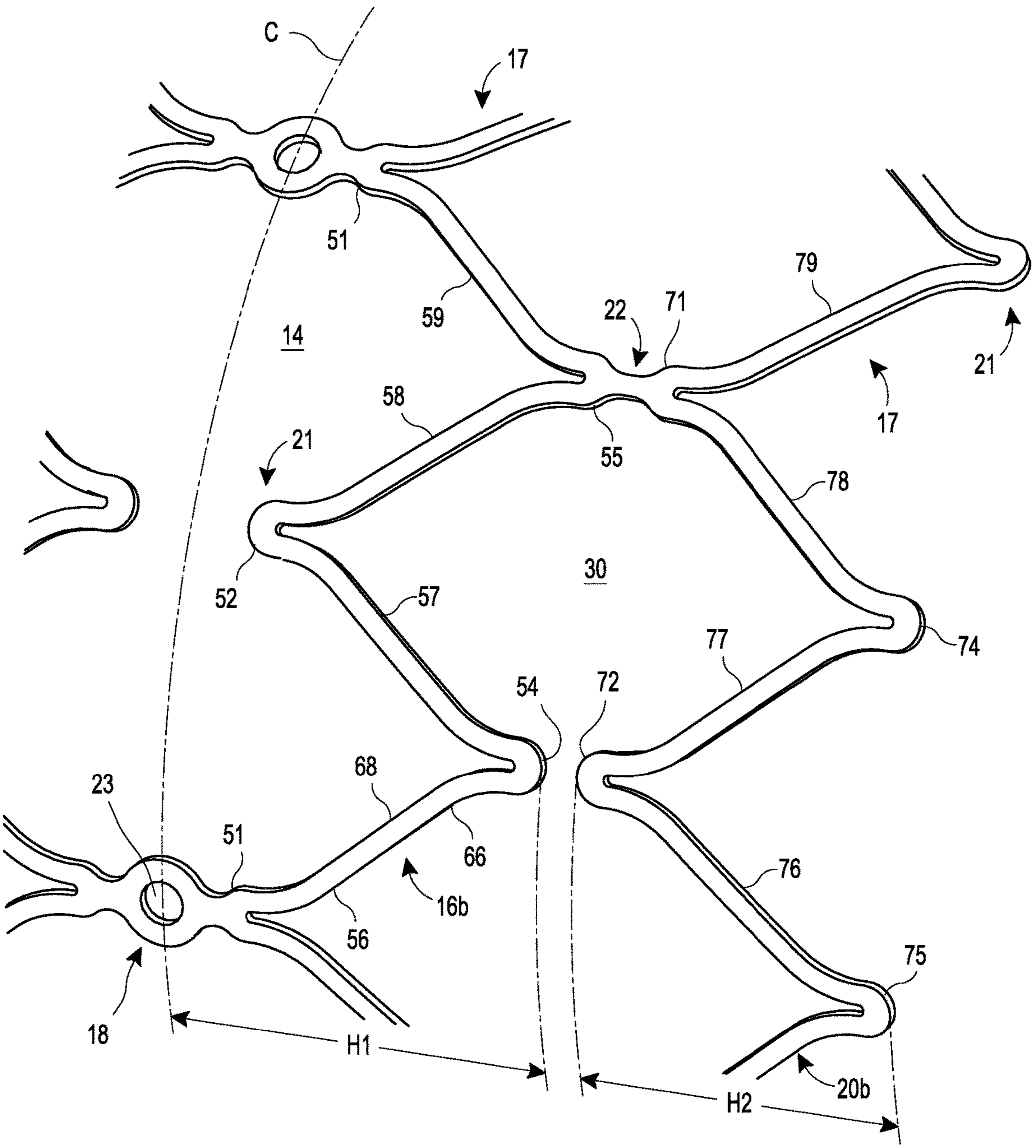
FIG. 4C shows a detail view of a section of the intravascular implant of FIGS. 4A and 4B.

With continued reference to FIGS. 4A-C, the implant 10 is shown having two outer rings 20*a,* 20*b* that are formed by a plurality of struts 17 connected by loops 21 (also referred to herein as "apexes") to form in a zig-zag pattern similar to the two inner rings 16*a,* 16*b*. The two outer rings 20*a,* 20*b,* can be referred to as the third and fourth rings 20a, 20*b* of the implant 10 or also as the distal outer ring 20*a* and the proximal outer ring 20*b* of the implant 10. Each outer ring 20*a,* 20*b* can be joined by outer bridges 22 that connect each outer ring 20*a,* 20*b,* to the adjacent inner ring 16*a,* 16*b*. The adjacent inner rings 16*a,* 16*b*, outer rings 20*a,* 20*b,* and outer bridges 22 define peripheral columns of bounded peripheral cells 30 along an outer surface of the implant. The boundary of each of the peripheral cells 30 can made up of a number of outer bridge 22 or struts 17. As shown, each outer ring 20*a*, 20*b,* can be a mirror image of the respective inner ring 16*a,* 16*b* that it is connected to. Also shown, the two outer rings 20*a,* 20*b* can be mirror images of each other. The outer rings 20*a*, 20*b,* can also be considered coaxial, similar to the inner rings 16*a,* 16*b*. Similar to the inner bridges 18, the outer bridge 22 can be symmetrical across a transverse plane extending through the axial mid-point thereof, though other configurations are also possible.

FIG. 4C is a closer view a portion of the intravascular implant 10 illustrating a portion of the central cells 14 and a portion of a boundary thereof as well as a portion of the peripheral cells 30 and a portion of a boundary thereof. The portion illustrated to the right of the midline C is one half of the central cell 14 and the peripheral cell 30 in one embodiment. The other half can be a mirror image, as shown in FIGS. 4A-B, an inverted mirror image, or some other configuration. The portion of the ring 16*b* that is part of an individual central cell 14 can define a portion that is repeated in a pattern along the inner ring 16*b*. Similarly, the portion of the outer ring 20*b* that is part of an individual peripheral cell 30 can define a portion that is repeated in a pattern along the outer ring 20*b*. In some embodiments, the inner rings 16*a,* 16*b* and the outer rings 20*a,* 20*b* can have portions that are repeated in a pattern that extends across the central cells 14 or peripheral cells 30, such as across 1.5 cells, 2 cells, 3, cells, etc. The pattern of the inner rings 16*a,* 16*b* and outer rings 20*a,* 20*b,* combined with other features of the implant 10 can enable it to be circumferentially compressible. The difference between the compressed and expanded states can be seen by comparing the compressed view shown in FIG. 4A and the expanded view shown in FIG. 4B.

The central cells 14 of the implant 10 can be bounded by portions of two rings 16*a,* 16*b,* which can be mirror images of each other. Similarly, the peripheral cells 30 of the implant 10 can be bounded by portions of the inner ring 16*a,* 16*b* and outer rings 20*a*, 2*b,* which can be mirror images of each other. Thus, some embodiments can be fully described by reference to only one side of the implant 10 and of the central cell 14 and one of the outer cells 30. The inner ring 16*a,* 16*b* and outer ring 20*a,* 20*b,* portions of which are illustrated in FIG. 4C, have an undulating sinusoidal pattern. The undulating pattern can have a single amplitude configuration shown but in other embodiments can have more than one amplitude. The patterns and frequency of the inner ring 16*a,* 16*b* and outer ring 20*a,* 20*b* can be the same, such as in the configuration shown. The patterns of the inner ring 16*a,* 16*b* and outer ring 20*a,* 20*b* can also differ.

With continued reference to FIG. 4C the inner rings 16*a,* 16*b* can have a plurality of struts 17 sections of which are labeled individually as struts 56, 57, 58, 59. The plurality of struts 17 can repeat about the circumference of the inner rings 16*a,* 16*b*. The struts 17 can be many different shapes and sizes. The struts 17 can extend in various different configurations. In some embodiments, the plurality of struts 56, 57, 58, 59 extend between inner and outer loops (also referred to as "apices") 21, which are labeled as inward apices 51, 52 and outward apices 54, 55 in FIG. 4C. In several embodiments of the implant 10, the struts can have a strut width of about 0.120 mm to about 0.160 mm and in an embodiment about 0.120 mm to about 0.165 mm and in an embodiment about 0.142 mm. In several embodiments, the implant 10 can have a strut length of about 2.00 mm to about 2.2 mm and in an embodiment a strut length of about 2.138 mm.

In some embodiments, the outward apices 54, 55 can extend axially similar or same distances as measured from a central zone or midline C of the implant 10. Similarly, the inward apices 51, 52 may be axially aligned, e.g., being positioned at the same or similar axial distance from the midline C.

The inner bridges 18 can be connected to one or more of the inward apices 51, 52. The inner bridges 18 can join the two inner rings 16*a*, 16*b* together. The bridge 18 can have many different shapes and configurations. A mentioned above, the bridge 18 can be located at the central zone or midline C of the implant 10. In FIGS. 4-C, the word "proximal" refers to a location on the implant 10 that would be closest to vascular access site than the portion labeled "distal". However, the implant 10 can also be thought of as having a medial portion that corresponds to the midline C and lateral portions extending in both directions therefrom. As such, the location labeled "proximal" is also a medial location and the location labeled "distal" is also a lateral position. All of these terms may be used herein.

As shown, the bridge 18 is connected to each ring at the inward apex 51. In some embodiments, a bridge 18 is connected to every inward apex, forming a closed cell construction. In other embodiments, as shown in FIGS. 4A-C, the bridge 18 is connected to every other inward apex. The remaining inward apexes can be unconnected. In other embodiments, the bridge 18 can connect every third inward apex, or spaced farther apart by as needed, forming a variety of open cell configurations. The number of bridges 18 can be chosen depending upon the application. For example, six or fewer bridges 18 may be used between the two rings 16*a*, 16*b*.

Similar to the two inner rings 16*a*, 16*b*, the outer rings 20*a*, 20*b* can have a plurality of struts 17 sections of which are labeled 76, 77, 78, 79 in FIG. 4C. The plurality of struts 17 can repeat about the circumference of the outer ring 20. The struts can be many different shapes and sizes. The struts can extend in various different configurations. In some embodiments, the plurality of struts 76, 77, 78, 79 extend between inward apices (also referred to herein as loops) 71, 72 and outward apices (also referred to herein as loops) 74, 75.

In some embodiments, the outward apices 74, 75 can extend axially similar distances as measured from a central zone or midline C of the implant 10. Similarly, the inward apices 71, 72 may be axially aligned, e.g., being positioned at the same axial distance from the midline C.

In some embodiments, the axial length of the implant 10 is measured from the top of the outward apex 74 on the distal side of the proximal cell 30 to the corresponding top of the outward apex 74 on the proximal side of the other proximal cell 30. In certain embodiments, the implant 10 has an axial length of between 8-12 mm in one embodiment or 10-11 mm in another embodiment and 10.4 mm in another embodiment.

The outer bridges 22 can join one or more outward apices 54, 55 of the inner ring 16 with one or more inward apices 71, 72 of the outer ring 20*a*, 20*b*. The outer bridges 22 thus can join the inner rings 16*a*, 16*b* with the adjacent outer ring 20*a*, 20*b*. The outer bridge 22 can have many different shapes and configurations. In the illustrated embodiment, the outer bridges 22 comprise a straight bridge that connects opposing apexes.

As shown, the outer bridges 22 connect the outward apex 55 of the inner ring 16 with the inward apex 71 of the outer ring 20. In some embodiments, the outer bridges 22 are connected to every inward apex, forming a closed cell construction. In other embodiments, as shown in FIGS. 4A-D the connection 22 is connected to every other outward apex 55 of the inner ring 16 with the inward apex 71 of the outer ring 20. The remaining apexes can be unconnected. In other embodiments, every third outward apex 55 and inward apex 71 are connected, or spaced farther apart by as needed, forming a variety of open cell configurations. The number of connections 22 can be chosen depending upon the application. For example, six or fewer bridges 22 may be used between the two rings 16*a*, 16*b*.

In some embodiments, as shown in FIGS. 4A-4D the bridges 18 of central column may be aligned with the connections 22 of the peripheral columns. In some embodiments, the bridges 18 of the central columns may alternate with the connections 22 of the peripheral columns. Put another way, the same individual strut or structural member 59 of the inner ring 16 may be joined by the bridge 18 at the proximal end of the individual strut 59 and joined by the outer bridges 22 at the distal end of the individual strut 59. The alternating pattern of the bridges (formed with every other inward apex of the inner ring) as described above can also increase flexibility of the implant. Similarly, the alternating pattern of the connections (formed with every other inward apex of the outer ring and every other outward apex of the inner ring) as described above can also provide increased flexibility of the implant.

The apices 51, 52, 54, 55, 71, 72, 74, 75 can have higher or increased width. The higher material apices can minimize the gaps between struts when the implant 10 is crimped. The higher material apices can also provide increased stability of the structure and increased radial force of the overall implant design.

Figure 4D:
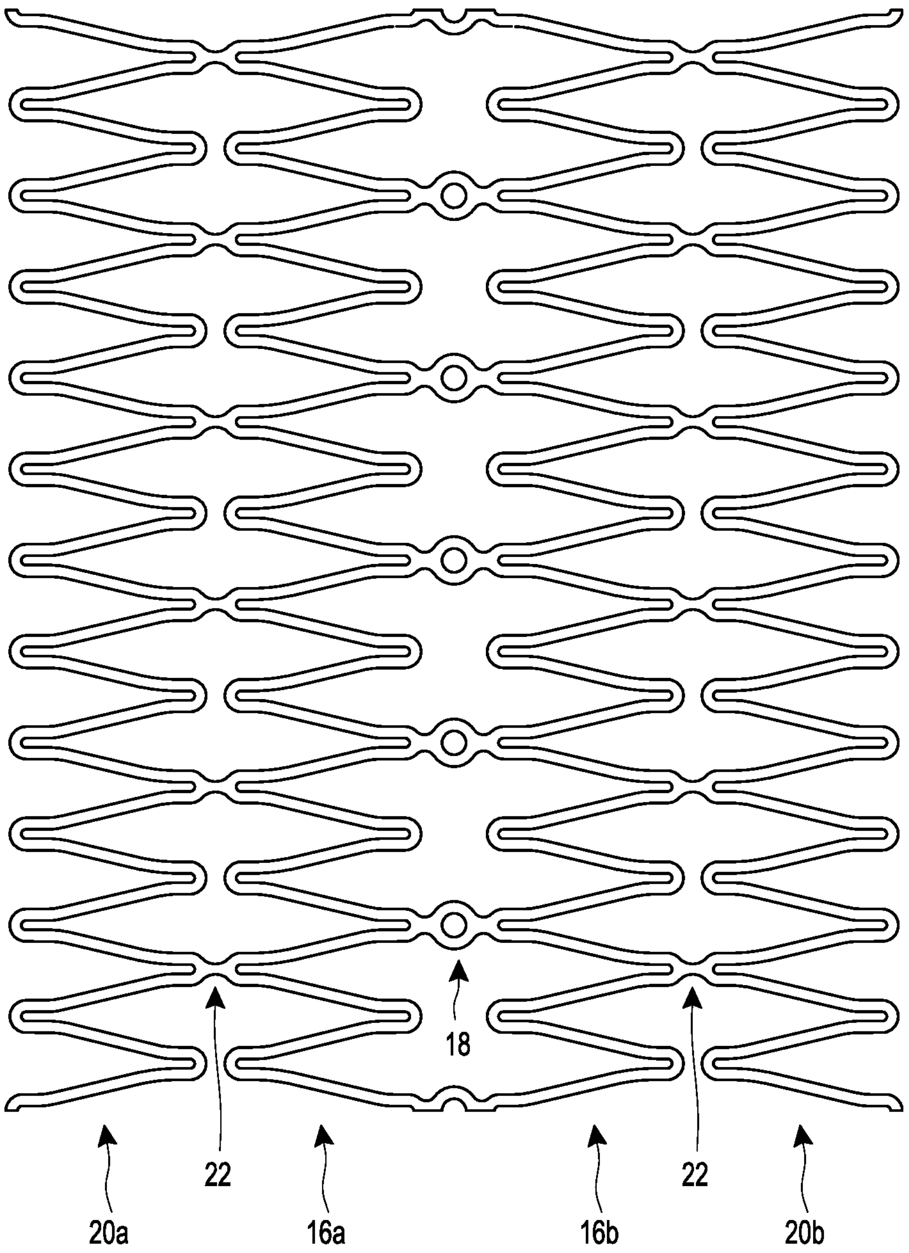
FIG. 4D illustrates the pattern of the intravascular implant of FIGS. 4A-C illustrating the implant rolled out into a flat configuration.
Figure 4F:
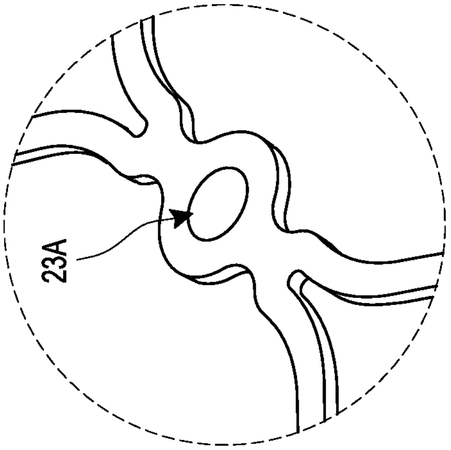
FIG. 4F illustrates an enlarged portion of FIG. 4E.
Figure 4E:
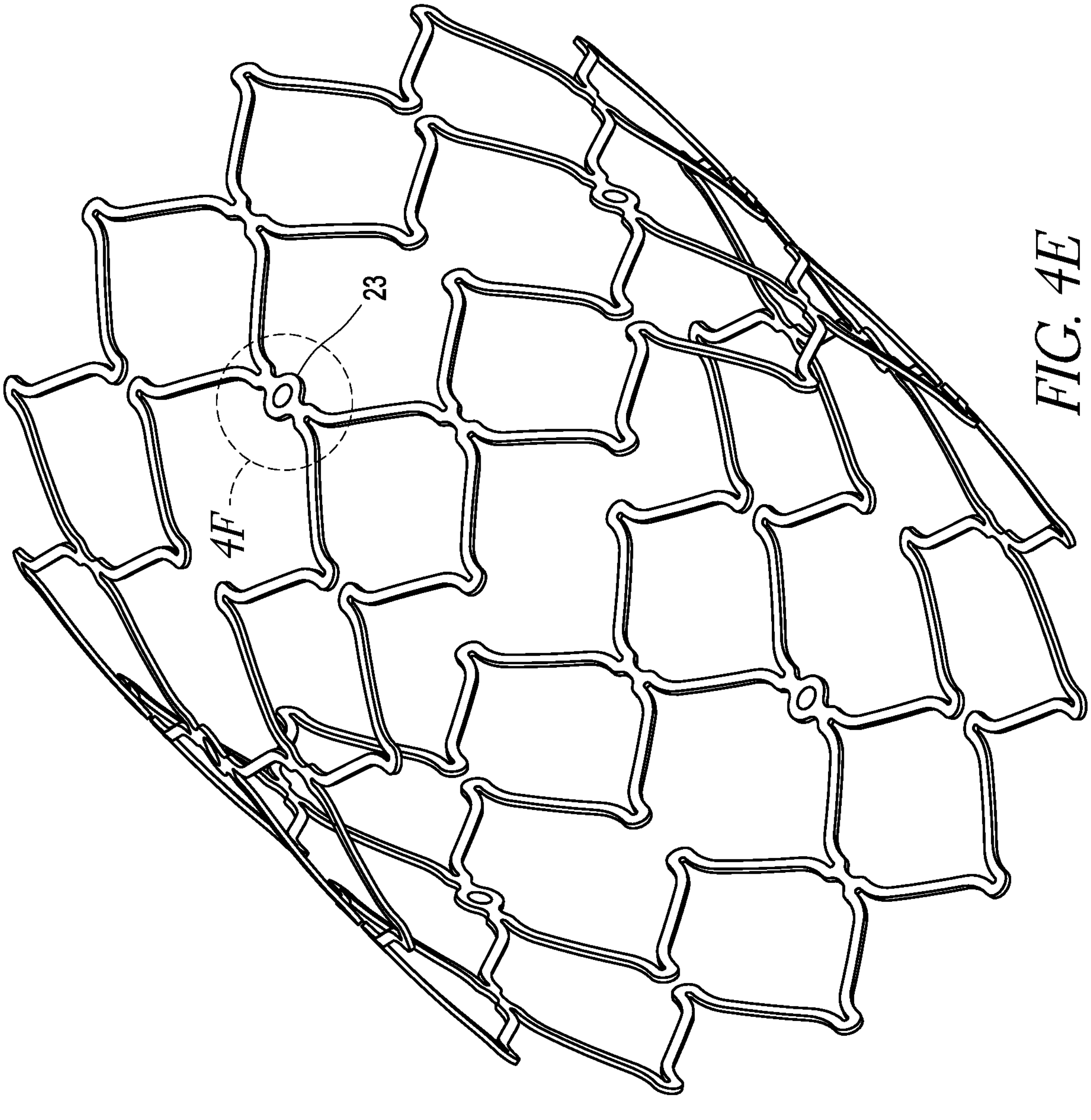
FIG. 4E illustrates the embodiment of an intravascular implant shown in FIG. 4B with markers.

FIG. 4D is illustrates the pattern of the intravascular implant 10 of FIGS. 4A-C by showing the implant 10 rolled into a flat pattern so as to emphasized certain features according to certain embodiments. In particular, in the illustrated arrangement, the outer bridges 22 and inner bridges 18 alternate as described above (formed with every other facing apices of adjacent rings). In addition, as shown in FIG. 4D, the inner bridges 18 alternate with respect to the outer bridges 22 such that the alternating inner bridges 18 are located circumferentially between the alternating outer bridges 22. As shown in FIGS. 4B and 4C, the struts 17 can include inflection points along the length of the struts near the apexes 21.

Column Cell Design

An aspect of the embodiment of the intravascular implant 10 of FIGS. 4A-C is that it can comprise a triple column open cell design with the one central column between two inner zig-zag rings and two peripheral columns between two additional zig-zag rings on either side of the inner zig-zag rings. This arrangement can advantageously provide reduced metal burden scaffolding of a vessel while also providing a relatively high radial force. In an embodiment, the implant 10 can consist of a triple column open cell design with one central column between two inner zig-zag rings and two peripheral columns between two additional distal-most and proximal-most zig-zag rings on either side of the inner zig-zag rings.

In an embodiment, a ratio of the vessel contact area to the total treatment zone of the implant 10 can be kept small while still achieving certain force characteristics as described herein. In this manner, the implant 10 can be designed to have substantially less metal coverage and/or contact with the blood vessel surface, thereby inciting less acute and chronic inflammation. Reduced contact area of implanted material against the blood vessel wall has been correlated with a lower incidence of intimal hyperplasia and better long-term patency. In this context, vessel contact area can be the sum of the area of outer surfaces of the implant 10 that may come into contact with the vessel wall. More particularly, the vessel contact area may be calculated as a summation for all of the struts of the length of each strut times the average transverse dimension (width) of the radially outer surface of each strut. The vessel contact area may also include the radially outer surface of the bridges 18, 22 and any markers 23A within the bridge. The total treatment zone of the implant 10 can be defined with respect to the fully expanded unconstrained configuration in a best fit cylinder. A best fit cylinder is one that has an inner circumference that is equal to the unconstrained fully expanded outer diameter circumference of the implant 10. The total treatment zone has an area that is defined between the proximal and distal ends (or the lateral edges) of the implant 10. The total treatment zone can be calculated as the length between the proximal and distal ends (or lateral edges) in the best fit cylinder times the inner circumference of the best fit cylinder. In the illustrated embodiment, the length for purposes of determining the total footprint can be the distance at the same circumferential position between high outward apices 74 of the rings 20.

In embodiments, the ratio of the vessel contact area to total treatment zone is less than 50%. In some embodiments, the ratio of the vessel contact area to total treatment zone is even less, e.g., 40% or less. The ratio of the vessel contact area to total treatment zone can be as small as 20% or less. In specific examples, the ratio of the vessel contact area to total treatment zone is 5% or even 2% or less. In embodiments, the ratio of the vessel contact area to total treatment zone is between 50% and 5%. In some embodiments, the ratio of the vessel contact area to total treatment zone is between 40% and 5%. The ratio of the vessel contact area to total treatment zone can be between 20% and 5% less. In embodiments, the implant 10 can have a total vessel contacting area of between 35 $mm^2$ and 40 $mm^2$ with an unconstrained length of between 8 and 12 mm with an unconstrained outer diameter between 8 mm and 12 mm.

In certain methods, a vessel can be treated by implanting a plurality of implants 10. The structures have a total contact area with the vessel wall. The total contact area may be the sum of the vessel contact area of the individual implants. In the method, a total treatment zone area can be defined as the surface area between the proximal end of the most proximal implant and the distal end of the distal most implant. In one method, the total contact area is no more than about 55% of the total treatment zone area. In an embodiment, the total contact area is between about 10% and about 30% of the total treatment zone area. In specific examples, the total contact area is no more than 5-10% of the total treatment zone area.

In some embodiments, the open area bounded by lateral edges of the implant 10 dominates the total footprint, as defined above. The open area of the implant 10 can be defined as the sum of the areas of the cells 14, 30 when the implant 10 is in the fully expanded configuration, as defined above. The open area can be calculated at the outer circumference of the implant 10, for example the area extending between the internal lateral edges of each of the struts. In this context, internal lateral edges are those that form at least a part of the boundary of the cells 14, 30. In various embodiments, the sum of the radially outwardly facing surface of the struts of the implant 10 can be no more than about 25% of the open area of the implant 10. The sum of the radially outwardly facing surface area of the implant 10 can be between about 10% to about 20% of the open area of the implant 10. In other examples, the sum of the radially outwardly facing surface of the struts of the implant 10 is less than about 2% of the open area of the implant 10.

A triple column design includes arrangements in a plurality of implant cells are oriented circumferentially about a central axis of the implant 10. Implant cells can come in many configurations, but generally include spaces enclosed by struts and are disposed in the wall surface of the implant. Open cell designs include arrangements in which at least some of a plurality of internally disposed struts of proximal and distal circumferential members are not connected by bridges or axial connectors. FIG. 4C shows that the inward apex 52 is unconnected to a corresponding inward apex on a mirror image ring 16. Thus, a portion of the cell 14 disposed above the inward apex 52 in FIG. 4C is open to another portion of the cell 14 disposed below the inward apex 52. Open cell designs can have increased flexibility and expandability compared to closed cell designs, in which each internally disposed struts of a proximal circumferential member is connected to a corresponding internally disposed struts of an adjacent circumferential member. The cell 14 would be divided into two closed cells by connecting the inward apex 52 to a corresponding inward apex on the mirror image ring 14. As discussed above, closed cell plaque implants can be suitable for certain indications and can include other features described herein. As shown, the single column open cell design extends along the midline C of the bridge (and also, in this embodiment, along the circumference of the implant 10).

In one embodiment, the cell 14 is identical to a plurality of additional cells 14 that would be disposed circumferentially about the central axis of the implant 10. The number of cells can vary depending on factors such as the size of the vessel(s) for which the implant 10 is configured, the preferred arrangements of the rings 16, the number of bridges 18 to be provided and other factors.

As discussed above, the intravascular implant 10 can include proximal and distal inner rings 16*a*, 16*b* connected by bridges 18. The bridges 18 can divide an outer surface of the implant 10 into inner or central cells 14 bounded by the bridges 18 and a portion of each of the proximal and distal inner rings 16*a*, 16*b*. The implant 10 can also include proximal and distal outer rings 20*a*, 20*b* joined to the inner rings 16 by outer bridges 22. The outer bridges 22 can divide an outer surface of the implant 10 into outer or peripheral cells 30 bounded by the outer bridges and a portion of each of the proximal and distal outer rings 20*a*, 20*b* and each of the corresponding proximal and distal inner rings 16*a*, 16*b*. For example, in FIG. 4C, the peripheral cell 30 shown is bounded by the proximal inner ring 16*b* and proximal outer ring 20*b*.

In the embodiment of FIGS. 4A-4D, the implant 10 with a triple column design is provided by providing bridges at only one axial position and a pair of circumferential inner members or inner rings 16*a*, 16*b* as well as a pair of circumferential outer members or outer rings 20*a*, 20*b* positioned on either end of the implant 10. Each circumferential outer ring 20*a*, 20*b* can be positioned on either end of the proximal and distal inner rings 16*a*, 16*b*. A first outer ring or circumferential outer member 20*b* can be positioned proximally to the proximal inner ring 16*b*. A second circumferential ring 20*a* can be positioned distally to the distal inner ring 16*a*. The proximal outer ring 20*b* can be disposed at a proximal end of the implant 10. The distal outer ring 20*a* can be disposed at a distal end of the implant 10. In some embodiments, the distal outer ring 20*a* is the distal most aspect of the implant and the proximal outer ring 20*b* is the proximal most aspect of the implant 10.

As discussed above, the cells 14, 30 can have one of many different shapes and configurations. FIG. 4B shows that, the cells 14 are aligned as a repeating pattern forming a single column of the triple column open cell design along the circumference of the implant. Similarly, the outer cells 30 can be aligned as a repeating pattern forming two peripheral columns of the triple column open cell design. Similarly, the circumferential members 16*a*, 16*b*, 20*a*, 20*b* can be aligned such that the inner and outer apices are aligned with each other.

The implant 10 with a triple column cell design can provide different features as compared to a single column cell design. The triple column cell design can provide increased structural integrity for a larger implant diameter and/or larger implant working diameter range, which can be used to treat larger vessels and/or to treat a larger range of vessels. The design can also provide for an increased length of implant 10. The design can also provide for an increased surface area of the implant 10. Additionally, the triple column cells can aid in providing a larger radial force and/or other force characters which will be described more below. These features of the triple column cells can provide more stability in larger vessels and can aid in treatment of more calcified lesion areas and dissections. While the illustrated implant 10 is shown with a triple column cell design, in certain aspects of the disclosure can be used with implants having more or less columns of cells.

The implant 10 may be crimped down to a compressed form. The compressed diameter may be adequately reduced and sized to fit within a 6 French catheter or any other desired catheter. As noted above, the implant 10 can be self-expanding.

Additionally, the triple column cell design may be adequately flexible and reduced in size to be maneuvered through tight bend radiuses. The symmetry of the design, such as the circumferential alignment of the four circumferential members, can help reduce the crimping size such that the implant may reach a desired compressed size. The circumferential alignment of the circumferential members can also increase flexibility to aid with the expansion when the implant 10 is deployed and positioned within a vessel.

In the embodiments described above, the intravascular implant 10 can have an unconstrained axial length of between 8 to 12 mm in some embodiments or between 10 to 11 mm in some embodiments and about 10.4 mm in some embodiments. In the embodiments described above, the implant 10 can also self-expand between diameters between at least 1.65 to 10 mm in some embodiments, between 2 to 10 mm in some embodiments or between at least 3 to 9 mm in some embodiments and between at least 4 to 8 mm in some embodiments. In several embodiments, the implant has between 10 columns and 3 columns of cells, in another embodiment, between 5 and 3 columns of cells, and in an embodiment only 3 columns of cells and in an embodiment 4 columns of cells.

Conventional stent designs are generally relatively long (e.g., 4 cm and even up to 20 cm when used in peripheral vasculature) from their distal to proximal ends. Where arranged with circumferentially disposed cells, conventional stents have a large number of columns of cells. These designs are burdened with repeating points of weakness and can generate stresses that become difficult to manage. As the device is put under stress and strain, these conventional stents must find regions of greater pliability within the strut matrix. These strut regions absorb the load throughout the system and under periods of repeated external forces begin to fail, such as through cyclical stress variations or metallurgical friction loading.

Embodiments of the implant 10 advantageously balance providing sufficient outward radial force to hold loose plaque and/or arterial tissue (dissections) against a blood vessel wall while also advantageously having sufficient radial force to be able to treat residual stenosis in non-calcified, moderately calcified or severely calcified lesions while remaining relatively short with relatively few columns. This reduces the repeated weak point loading due to movement of remote stent portions because the implant does not have to be axially elongated to provide effective treatment. Other benefits that derive from the shortness and the few columns are the reduced friction at the interface with the catheter sheath during delivery and with the blood vessel wall. Any motion between the surfaces of the implant and the blood vessel can cause rubbing and friction. If the motion is very small it can be described as micro-rubbing. Even micro-rubbing can produce a negative effect on both the implant 10 and the biological cells of the blood vessel. For example, friction occurs when a portion of an implanted object moves while another portion is stationary or moving by a smaller amount. Differential amounts of moving over time weakens the material leading to fracture by processes such as work hardening. The biological cells become irritated by the friction and can respond by producing an inflammation response Inflammation can drive a variety of undesired histological responses including neointimal hyperplasia and restenosis.

In any of the embodiments herein described, the implant 10 can be made from Nitinol. In several embodiments, the implant 10 can be from other materials such as silicon composite (with or without an inert coating), polyglycolic acid, or some other superelastic material, as well as stainless steel, tantalum, a cobalt chromium alloy, bioabsorbable or bioresorbable materials (including bioabsorbable/bioresorbable metals) or a polymer. The implant 10 can be cut from a tube, formed from strip of material, or can be created from ribbon, round or rectangular wire or a sheet of material processed through photolithographic processing, laser or water cutting, chemical etching or mechanical removal of the final shape, or the use of bottom up fabrication, for instance chemical vapor deposition processes, or the use of injection modeling, hot embossing, or the use of electro or electroless-plating. The implant 10 can be fabricated from metal, plastic, ceramic, or composite material.

Force Curve

Figure 5A:
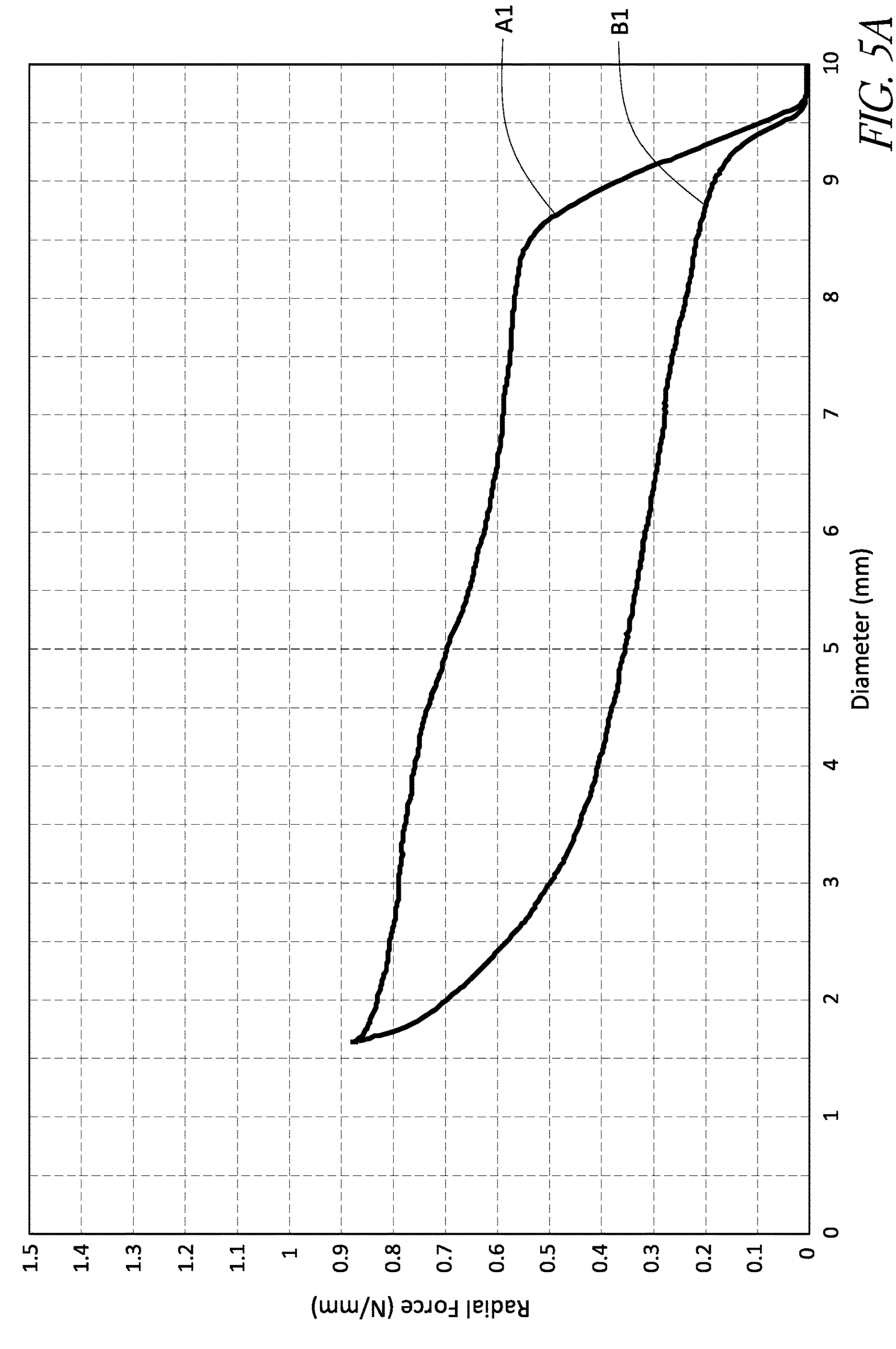
FIG. 5A is a chart illustrating the radial expansion forces according of an intravascular implant according to aspects of the present disclosure.
Figure 5B:
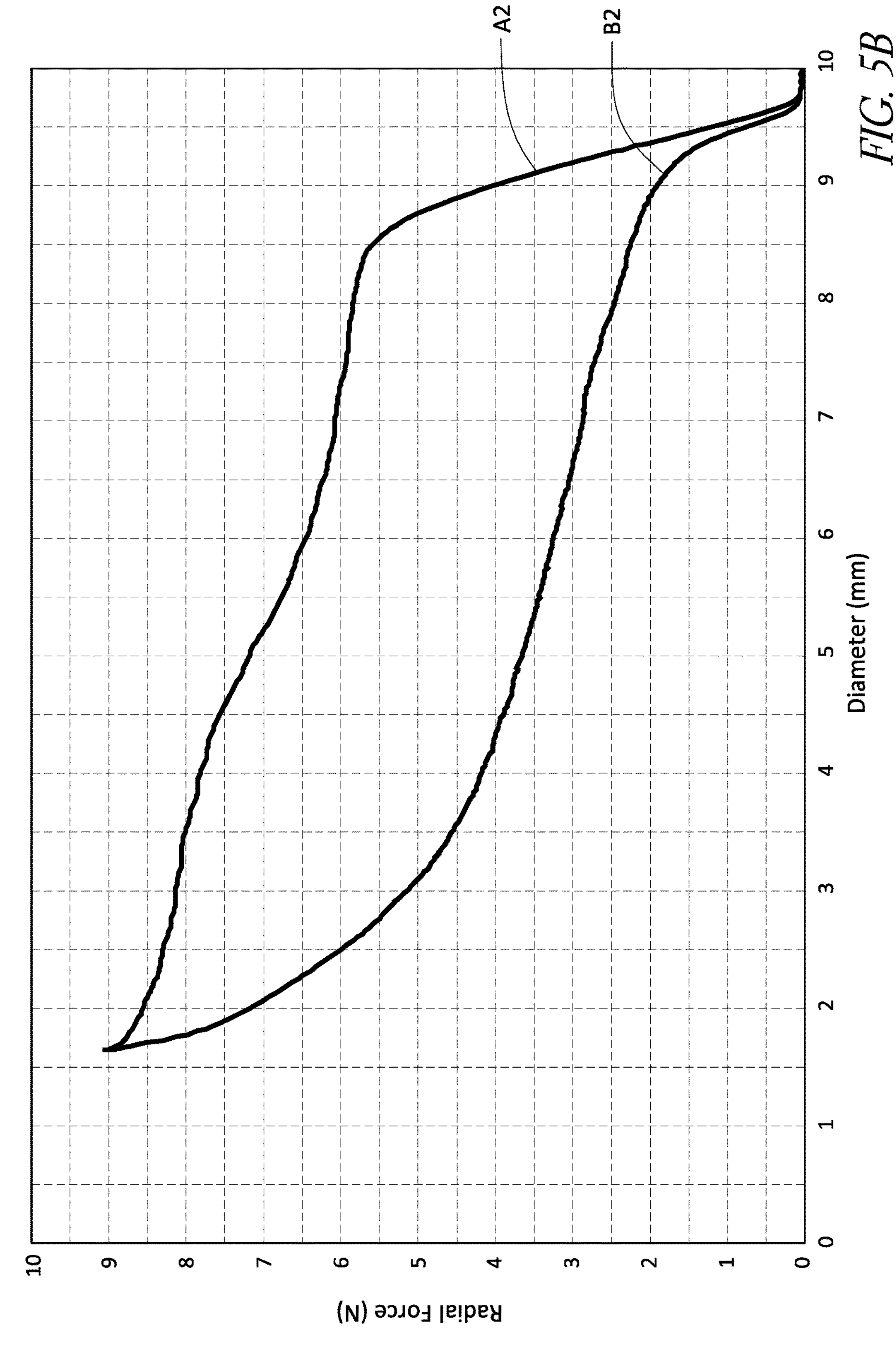
FIG. 5B is another chart illustrating the radial expansion forces according of an intravascular implant according to aspects of the present disclosure.

Another aspect of the intravascular implant 10 according to certain embodiments disclosed herein is that it can be configured to produce a force curve with an extended area having a low slope. Advantageously the implant 10 can be configured to produce a sufficiently high radial force such that it can used to treat dissections and/or residual stenosis in more calcified lesions and in several embodiments to treat calcified lesions in the peripheral arteries such as the SFA and proximal popliteal arteries. Advantageously, the implant 10 can be configured to both i) produce a force curve with an extended area having a low slope and ii) produce a sufficiently high radial force such that it can used to treat dissections and/or residual stenosis in more calcified lesions. FIGS. 5A and 5B illustrate force curves according to one or more of the embodiments of the implant 10 described above. The force curves in FIG. 5A and 5B illustrate the amount of force exerted by a self-expanding implant 10 when moving between a compressed state and an expanded state. The radial force of a device can be a factor in choosing the correct device to be placed in a particular blood vessel. One advantage to having a force curve with an extended area having a low slope in force as the device is expanding is the ability to predict the energy that the blood vessel experiences independent of the lumen diameter. Another value would be the reduction of necessary inventory for hospitals as a single implant can be used to treat a large range of vessel diameters, which can reduce the need to provide multiple models of implants to treat the same range of vessel diameters.

Still referring to FIGS. 5A and 5B, the force curves of the intravascular implant having the wall pattern as described with reference illustrated in FIGS. 4A-4D are illustrated. However, other embodiments can utilize certain features and aspects of the force curves described below with an implant with a different wall pattern than that described above. The FIG. 5A chart shows the radial force in Newtons per millimeter length of the implant (N/mm) on the y-axis and the outer diameter of the device exerting the force in millimeters (mm) on the x-axis. For the Y-axis, the millimeter length of the implant is measured along the longitudinal axis of the implant from the distal end of the implant to the proximal end of the implant and in one embodiment the unconstrained length of the implant is 10.4 mm. As the implant is expanded or moved from the compressed state to the expanded state, the outer diameter increases. Self-expanding implants have a set amount of stored potential energy. When released, the potential energy is converted into kinetic energy as the internal forces try to restore the implant to its expanded shape. The kinetic energy can then have an impact on the blood vessel when the implant is implanted. Also, if the implant 10 is not fully expanded a generally constant force will be applied to the vessel wall that corresponds to the remaining potential energy stored in the implant 10.

FIG. 5A shows a first line Al showing the compression or radial resistive force of an implant 10 having an unconstrained outer diameter of 9.75 mm and having an unconstrained length of 10.4 mm. The first line Al shows the compression force, which is also referred to as the radial resistive force (RRF), as the implant is compressed from a diameter of about 9.75 mm to about 1.65 mm. After a gradual slope region between about 9.75 mm and about 8.5 mm, the slope of the compression force for each incremental reduction in diameter is greatly reduced, providing a narrow band of force required to fully compress the implant 10 from about 8.5 mm to about 1.65 mm. This portion of the force curve is relatively flat particularly given the magnitude of the radial force, meaning that the applied compression force does not greatly increase as the implant approaches its fully compressed state. The flatness of this curve may be particularly useful in that the radial force in this portion can be greater than 0.6 N/mm in certain embodiments and greater than 0.5 N/mm in certain embodiments and greater than 0.4 N/mm in certain embodiments. In certain embodiments, the compression force curve can remain between 0.6 N/mm and 1 N/mm as the implant 10 is compressed from about 8.5 mm to about 1.5 mm. In certain embodiments, the compression force curve remains between 0.4 N/mm and 1.25 N/mm as the implant 10 is compressed from about 8.5 mm to about 1.5 mm. In certain embodiments, the compression force curve remains between 0.5 N/mm and 1 N/mm as the implant 10 is compressed from about 8.5 mm to about 1.5 mm. In certain embodiments, the compression force curve remains between 0.3 N/mm and 1.25 N/mm as the implant 10 is compressed from about 8 mm to about 2 mm. In certain embodiments, the compression force curve remains between 0.5 N/mm and 1.0 N/mm as the implant 10 is compressed from about 8 mm to about 2 mm. In certain embodiments, the compression force curve remains between 0.4 N/mm and 1.25 N/mm as the implant 10 is compressed from about 8 mm to about 4 mm. In certain embodiments, the compression force curve remains between 0.5 N/mm and 1 N/mm as the implant 10 is compressed from about 8 mm to about 4 mm. In certain embodiments, the compression force curve remains between 0.5 N/mm and 0.9 N/mm as the implant 10 is compressed from about 8 mm to about 4 mm. In certain embodiments, the implant has a peak radial compression force of between 0.9 N/mm and 1.3 N/mm and in certain embodiments the peak radial compression force is about 1 N/mm.

The expansion force curve, which is also referred to herein as the chronic outward force (COF) curve, of the intravascular implant 10 upon expansion is illustrated by a second line B1 extending from about 1.65 mm of compressed diameter to about 9.5 mm of an unconstrained expanded diameter. Unconstrained diameter or unconstrained outer diameter as used herein refers to the outer diameter of the implant when it is unconstrained and fully self-expanded. The range through which an implant can self-expand can be referred to herein as an expanded diameter range. This portion of the curve can be thought of as the working portion, in which the force on the Y-axis is the force that the implant would apply to a vessel wall upon expansion. For example, if the implant 10 was deployed in a vessel lumen having a bore of about 5.0 mm, the outward force of the implant on the wall would be less than about 0.4 Newton per unit length (N/mm). The flatness of the expansion curve can be provided in a treatment range of the device, which in this embodiment is between 4 mm and 8 mm. In certain embodiments, in this treatment range of 4 mm and 8 mm, the expansion force in this portion can be greater than 0.25 N/mm but less than 0.50 N/mm and, in certain embodiments, in this treatment range between 4 mm and 8 mm, the expansion force in this portion is greater than 0.18 N/mm but less than 0.70 N/mm. In certain embodiments, the implant has a minimum expansion force of between 0.15 N/mm and 0.35 N/mm at maximum treatment diameter which in certain embodiments is between 7 and 9 mm and in certain embodiments about 8 mm. In certain embodiments, the implant has a minimum expansion force of about 0.25 N at maximum treatment diameter which in certain embodiments is between 7 and 9 mm and in certain embodiments about 8 mm.

As can be seen in FIG. 5A, in some embodiments of the implant 10, it can have a low slope of the compression and expansion force curves A1, B1 over at least 3 mm, at least 4 mm, at least 5 mm, at least 6 mm, at least 7 mm or at least 7.5 mm of outer diameter expansion range. For example, in one embodiment, the implant 10 can have a change in radial expansion or compression force of less than 0.3 N/mm over 4 mm outer diameter expansion range and in certain embodiments less than 0.35 N/mm over 4 mm outer diameter expansion range and in certain embodiments less than 0.4 N/mm over 4 mm outer diameter expansion range. In one embodiment, the implant 10 can have a change in radial expansion or compression force of less than 0.25 N/mm over a 4 mm outer diameter expansion range and in an embodiment less than 0.2 N/mm over a 4 mm outer diameter expansion range. In some embodiments, the implant 10 can have a change in radial expansion or compression force less than the above values but greater than at least 0.1 N/mm over a 4 mm outer diameter expansion range. For example, in an embodiment, the implant 10 can have a change in radial expansion or compression force between 0.4 N/mm and 0.1 N/mm over 4 mm outer diameter expansion range and in certain embodiments between 0.35 N/mm and 0.1 N/mm over 4 mm outer diameter expansion range and in certain embodiments between 0.3 N/mm and 0.1 N/mm over 4 mm outer diameter expansion range and in certain embodiments between 0.25 N/mm and 0.1 N/mm over 4 mm outer diameter expansion range.

In some embodiments, the implant 10 can have a change in radial expansion or compression force of less than 0.2 N/mm over a 4 mm outer diameter expansion range. These ranges can be applied to an implant having an expanded diameter greater than 7 mm and in certain embodiments greater than 8 mm. These ranges can be applied to an implant having an expanded diameter between 7 and 12 mm and in certain embodiments between 8 and 10 mm. In addition, these ranges can be applied to an implant 10 having compression force A1 less than 1 N/mm, and in certain embodiments less than 1.25 N/mm and/or an expansion force B1 greater than 0.18 N/mm in certain embodiments and greater than 0.25 N/mm in certain embodiments within the treatment range of the device which can in certain embodiments include 4 mm to 8 mm.

The intravascular implant 10 can be radially self-expandable through a range of at least about 4 mm, at least about 5mm, at least about 6 mm, at least about 7 mm, or at least about 7.5 mm while exhibiting a radial compression force of no more than 1.25 N/mm in certain embodiments or no more than 1 N/mm in certain embodiments at any point throughout the range. In such embodiments, the radial compression force can be greater than 0.5 N/mm within these ranges. The implant 10 can also be radially self-expandable through a range of at least about 4 mm, at least about 5 mm, at least about 6 mm, at least about 7 mm, or at least about 7.5 mm while exhibiting a radial expansion force of greater than 0.18 N/mm, greater than 0.20 N/mm, or greater than 0.24 N/mm at any point throughout the range. In such embodiments, the radial expansion force can remain below 1 N/mm. In several embodiments the implant 10 can be used to treat vessels have a dimeter between 4 mm and 8 mm.

In certain arrangements, the implant 10 is indicated for a treatment of vessels having a diameter that can range from 4.0 to 8.0 mm. With continued reference to FIG. 5A, within this range, in an embodiment, the maximum radial compression force throughout the expansion range is no more than 1.25 N/mm in certain embodiments, and in certain embodiments no more than 1 N/mm and can be no more than about 0.9 N/mm in certain embodiments. In one embodiment, the compression force A1 and/or the expansion force B1 drops no more than about 0.35 N/mm, and in certain embodiments no more than 0.3 N/mm, and in certain embodiments no more than 0.25 N/mm, and in certain embodiments no more than 0.20 N/mm within this treatment range of 4 to 8 mm. The difference between the radial force of compression A1 and the radial expansion force B1 at any given diameter throughout the treatment range of 4 mm to 8 mm is no more than about 0.4 N/mm in certain embodiments and no more than about 0.55 N/mm in certain embodiments. In one implementation, the implant 10 is expandable throughout the range of 4 mm through 8 mm and the difference between the compression force and expansion force at each point along the compression/expansion range differs by no more than about 0.4 N/mm.

In several embodiments, the outward force of the implant 10 can be kept to be as low as possible, while providing sufficient force to treat dissections of loose plaque or tissue and residual stenosis of more calcified lesion areas. Additionally, the implant 10 can advantageously be used in larger vessels and with increased radial force as compared to previous implant configurations. Although a very low force implant is preferred for the certain treatments, higher force implant may be useful where loose plaque is found at calcified lesions. The implant 10 here can also hold the plaque against the lumen wall through a wide range of luminal diameters. Elevated force is desirable to treat dissections in increased calcified lesions. However, it is also still desirable to reduce or minimize the force, as adverse side effects can occur within the vessel tissue. These can include irritating the cells of the vessel wall that are in contact with the device, which can lead to re-stenosis amongst other complications.

One advantage to having a low change in force as the device is expanding is the ability to predict the energy that the blood vessel experiences independent of the lumen diameter. Another value would be the reduction of necessary inventory for hospitals.

As noted above, an aspect of the implant 10 according to certain embodiments disclosed herein is that it can be configured to produce a force curve with an extended area having a low slope while also producing a sufficiently high radial force such that the implant can be used to treat dissections or residual stenosis in more calcified lesions. FIG. 5B illustrates a force curve according to one or more of the embodiments of the implant 10 described above. The force curve in FIG. 5B is for the same implant 10 as FIG. 5A. Like FIG. 5A, FIG. 5B illustrates the amount of radial force exerted by or on a self-expanding implant 10 when moving between a compressed state and an expanded state. However, other embodiments can utilize certain features and aspects of the force curves described below with an implant with a different wall pattern than that described above.

FIG. 5B shows the gross radial force in Newtons (N) for the entire implant (not adjusted for implant length as in FIG. 5A) on the y-axis and the outer diameter of the device exerting the force in millimeters (mm) on the x-axis. FIG. 5B shows a first line A2 showing the compression or radial resistive force of an implant 10 having an unconstrained outer diameter of 9.75 mm and having an unconstrained length of 10.4 mm. The first line A2 shows the compression force as the implant is compressed from a diameter of about 9.75 mm to about 1.65 mm. After a gradual slope region between about 9.75 mm and about 8.5 mm, the slope of the compression force for each incremental reduction in diameter is greatly reduced, providing a narrow band of force required to fully compress the implant 10 from about 8.5 mm to about 1.65 mm. This portion of the force curve is relatively flat particularly given the magnitude of the radial force, meaning that the applied compression force does not greatly increase as the implant approaches its fully compressed state. The flatness of this curve may be particularly useful in that the radial force in this portion can be greater than 4.0 N in certain embodiments greater than 5.5 N in certain embodiments, greater than 6 N in certain embodiments. In certain arrangements, the flatness of this curve may be particularly useful in that the radial force in this portion can be between 4.0 N and 13 N in certain embodiments and between 5.5 N and 10 N in certain embodiments. In certain embodiments, the compression force curve remains between 4 N and 10 N as the implant 10 is compressed from about 8.5 mm to about 1.5 mm. In certain embodiments, the compression force curve remains between 4 N and 13 N as the implant 10 is compressed from about 8.5 mm to about 1.5 mm. In certain embodiments, the compression force curve remains between 5 N and 10 N as the implant 10 is compressed from about 8 mm to about 4 mm. In certain embodiments, the compression force curve remains between 5 N and 9 N as the implant 10 is compressed from about 8 mm to about 4 mm. In certain embodiments, the compression force curve remains between 5 N and 8 N as the implant 10 is compressed from about 8 mm to about 4 mm. In certain embodiments, the implant has a peak radial compression force of between 9 N and 13 N and in certain embodiments the peak radial compression force is about 10 N.

The expansion force or chronic outward force (COF) curve of the implant 10 upon expansion is illustrated by a second line B2 extending from about 1.65 mm of compressed diameter to about 9.5 mm of an unconstrained expanded diameter. This portion of the curve can be thought of as the working portion, in which the force on the Y-axis is the force that the implant would apply to a vessel wall upon expansion. For example, if the implant 10 was deployed in a vessel lumen having a bore of about 5.0 mm, the outward force of the implant on the wall would be less than about 4 Newtons. The flatness of the expansion curve can be provided in a treatment range of the device, which in this embodiment is between 4 mm and 8 mm. In certain embodiments, in this treatment range of 4 mm and 8 mm, the radial force in this portion is greater than 2.5 N but less than 5 N and, in certain embodiments, in this treatment range between 4 mm and 8 mm, the radial force in this portion is greater than 2 N but less than 7.0 N. In certain embodiments, the implant has a minimum expansion force of between 1.5 N and 3.5 N at maximum treatment diameter which in certain embodiments is between 7 mm and 9 mm and in certain embodiments about 8 mm. In certain embodiments, the implant has a minimum expansion force of about 2.5 N at maximum treatment diameter which in certain embodiments is between 7 mm and 9 mm and in certain embodiments about 8 mm.

As can be seen in FIG. 5B, in some embodiments of the implant 10, it can have a low slope of the compression and expansion force curves A2, B2 over at least 3 mm, at least 4 mm, at least 5 mm, at least 6 mm, at least 7 mm, or at least 7.5 mm of outer diameter expansion range. For example, in one embodiment, the implant 10 can have a change in radial expansion or compression force of less than 3 N over 4 mm outer diameter expansion range and in certain embodiments less than 3.5 N over 4 mm outer diameter expansion range and in certain embodiments less than 4 N over 4 mm outer diameter expansion range and these ranges can be within the range of expansion between 4 mm and 8 mm. In several embodiments, the implant 10 can have a change in radial expansion or compression force of less than 2.5 N over a 4 mm outer diameter expansion range and in an embodiment less than 2N over a 4 mm outer diameter expansion range. In these embodiments, the implant 10 can have a change in radial expansion or compression force of greater than at least than 1 N over a 4 mm outer diameter expansion range. For example, in several embodiments, the implant 10 can have a change in radial expansion or compression between 4 N and 1 N over 4 mm outer diameter expansion range and in certain embodiments between than 3.5 N and 1 N over 4 mm outer diameter expansion range and in certain embodiments between 3 N and 1 N over 4 mm outer diameter expansion range and in certain embodiments between 2.5 N and 1 N and these ranges can be within the range of expansion between 4 mm and 8 mm. In some embodiments, the implant 10 can have a change in radial expansion or compression force of less than 1 N over a 4 mm outer diameter expansion range. These ranges can be applied to an implant having a fully expanded diameter greater than 7 mm and in certain embodiments greater than 8 mm. In certain embodiments, these ranges can be applied to an implant having a fully expanded diameter between 7 mm and 12 mm and in certain embodiments between 8 mm and 10 mm. In addition, these ranges can be achieved with the implant 10 having compression force A2 less than 10 N in certain embodiments less than 13 N and/or an expansion force B2 greater than 1.8 N in certain embodiments and greater than 2.5 N in certain embodiments within the treatment range of the device which can in certain embodiments include 4 mm to 8 mm.

The implant 10 can be radially self- expandable through a range of at least about 4 mm, at least about 5 mm, at least about 6 mm, at least about 7 mm, or at least about 7.5 mm while exhibiting a radial compression force of no more than 13 N in certain embodiments or no more than 10 N in certain embodiments at any point throughout the range. The self-expandable range can be referred to herein as the expanded diameter range of the implant. In such embodiments, the compression force can be greater than 5 N within these ranges and in several embodiments above 4N within these ranges. The implant 10 can also be radially self- expandable through a range of at least about 4 mm, at least about 5 mm, at least about 6 mm, at least about 7 mm, or at least about 7.5 mm while exhibiting a radial expansion force of greater than 1.8 N, greater than 2.0 N, or greater than 2.4 N at any point throughout the range. In such embodiments, the expansion force can remain below 10 N within these ranges.

As noted above, in certain arrangements, the implant 10 is indicated for a vessel treatment range of 4.0 mm to 8.0 mm. With continued reference to FIG. 5B, within this range, in an embodiment, the maximum radial compression force A2 throughout the expansion range can be no more than 13 N in certain embodiments, and in certain embodiments no more than 10 N and can be no more than about 9 N in certain embodiments. In an embodiment, the compression force A2 and/or the expansion force B2 drops no more than about 3.5 N, and in certain embodiments no more than 3 N, and in certain embodiments no more than 2.5 N, and in certain embodiments no more than 2 N within this treatment range of 4 mm to 8 mm. Within these ranges, the compression force A2 and/or the expansion force B2 can drop by at least 1 N and in certain embodiments by least 2 N. The difference between the radial force of compression A2 and the radial expansion force B2 at any given diameter throughout the treatment range of 4 mm to 8 mm, in certain embodiments, can be no more than about 4 N. In one implementation, the implant 10 is expandable throughout the range of 4 mm through 8 mm and the difference between the compression force and expansion force at each point along the compression/expansion range differs by no more than about 3.5 N/mm and in certain embodiments no more than about 4 N/mm.

In an embodiment, the outward force of the implant 10 can be kept to be as low as possible, while providing sufficient force to treat dissections of loose plaque and/or residual stenosis of more calcified lesion areas. Additionally, the implant 10 can advantageously be used in larger vessels and with increased radial force as compared to previous implant configurations. Although a very low force implant is preferred for the certain treatments, higher force implant may be useful where loose plaque is found at calcified lesions. The implant 10 here can also hold the plaque against the lumen wall through a wide range of luminal diameters. Elevated force is desirable to treat dissections in increased calcified lesions. However, it is also still desirable to reduce or minimize the force, as adverse side effects can occur within the vessel tissue. These can include irritating the cells of the vessel wall that are in contact with the device, which can lead to re-stenosis amongst other complications.

One advantage to having a low change in force as the device is expanding is the ability to predict the energy that the blood vessel experiences independent of the lumen diameter. Another value would be the reduction of necessary inventory for hospitals.

In the embodiments described above, the intravascular implant 10 can have an unconstrained axial length of between 8 mm to 12 mm in some embodiments or between 10 mm to 11 mm in some embodiments and about 10.4 mm in some embodiments. In the embodiments described above, the implant 10 can also have an expanded diameter range such that the implant can self-expand between diameters between at least 1.65 mm to 10 mm in some embodiments or between at least 3 mm to 9 mm in some embodiments and between at least 4 mm to 8 mm in some embodiments and within these ranges can have one or more of the force curve characteristics described above. In several embodiments, the implant 10 has between 10 columns and 3 columns of cells, in another embodiment, between 5 and 3 columns of cells, and in one embodiment only 3 columns of cells and in an embodiment 4 columns of cells. A column of cells can be defined as a pair of rings and each ring can be formed by series of struts and apexes that can form a repeating pattern in certain embodiments. In such embodiments, implants with one, two, three, or four columns of cells can be formed by two, three, four or five rings respectively.

C. Method and Devices for Delivering Implants and Forming Intravascular Constructs In Situ A variety of delivery methodologies and devices can be used to deploy embodiments of the implants described herein, some of which are described below. For example, the implant 10 according to any of the embodiments described herein can be delivered into the blood vessel with an endovascular insertion. The delivery catheters for the different embodiments of implants can be different or the same and can have features specifically designed to deliver the specific implant.

Figure 6:
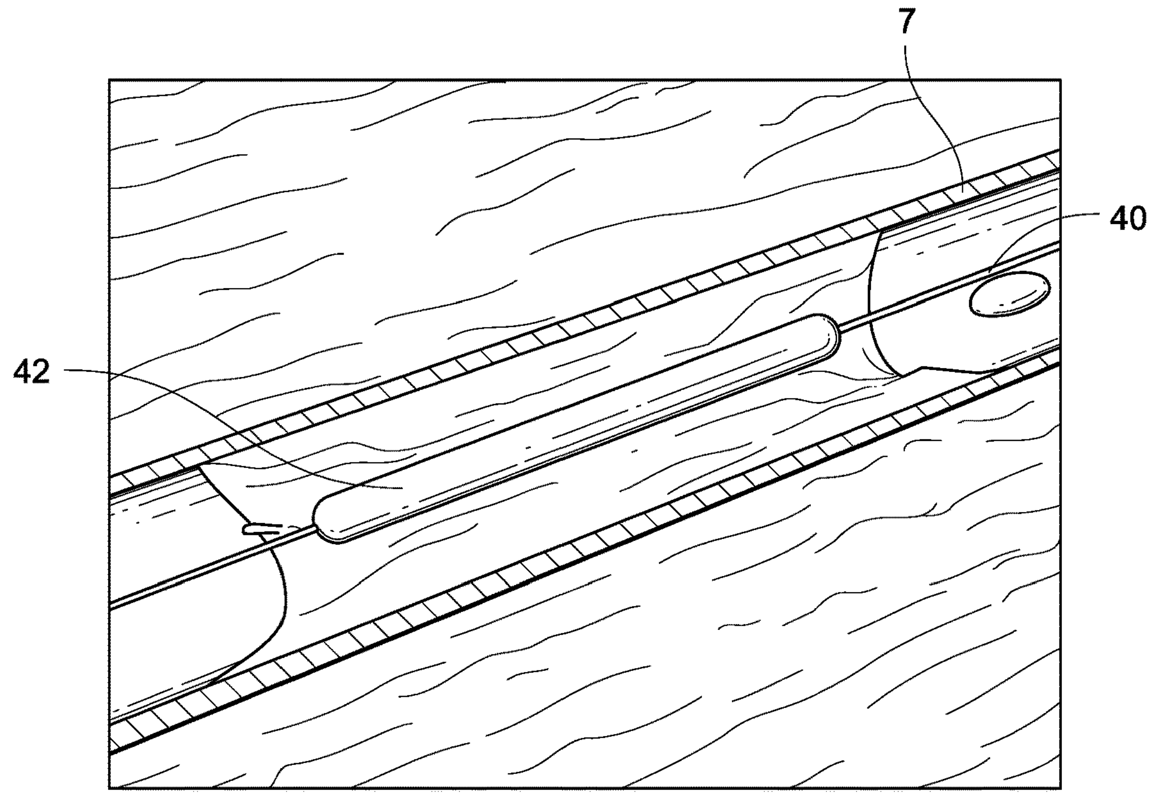
FIGS. 6-12 illustrate a method of treatment site preparation and delivery of an implant into a blood vessel.
Figure 7:
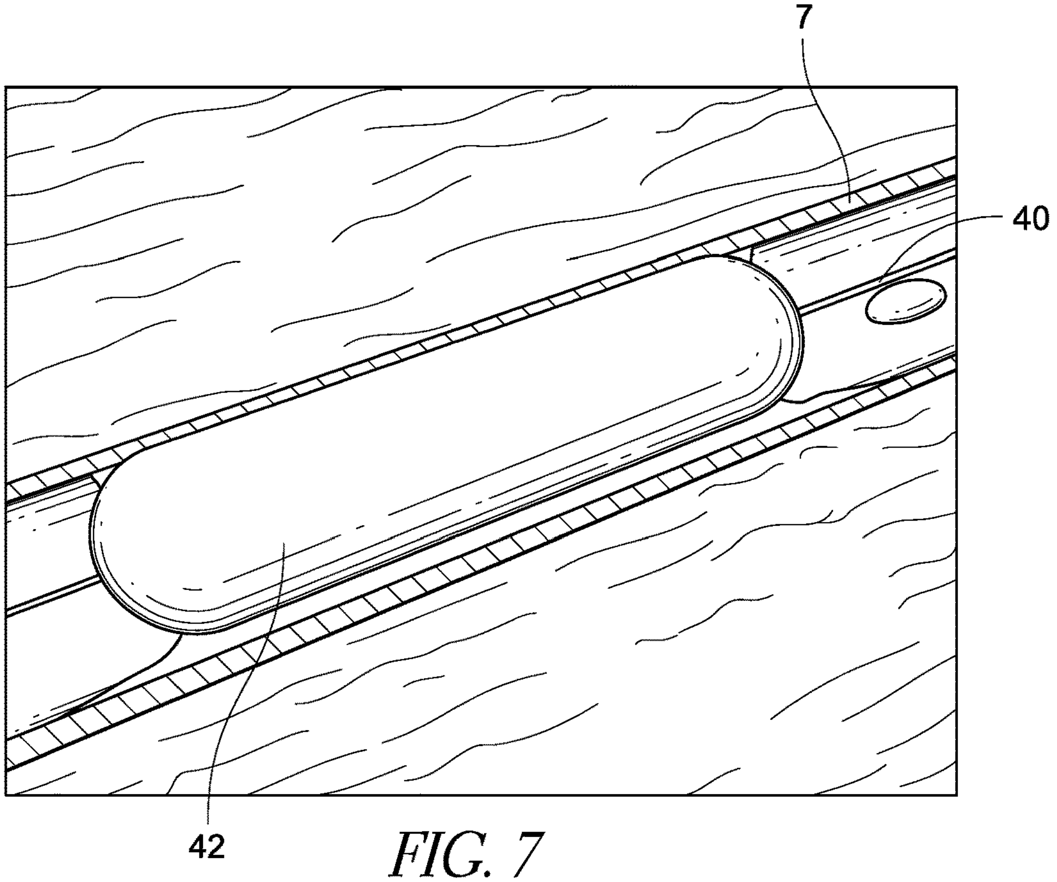

Turning now to FIGS. 6-12, a method of delivery of one or more intravascular implants 10 which can be configured as described in this disclosure will be described. The method can utilize embodiments of the delivery catheter 1 described above with reference to FIGS. 1-3A described above. As has been mentioned, an angioplasty procedure or other type of procedure can be performed in a blood vessel 7. The angioplasty may be performed on a diseased or obstructed portion of the blood vessel 7. The diseased vessel can first be accessed with a cannula, and a guidewire 40 advanced through the cannula to the desired location. As shown in FIG. 6, an angioplasty balloon catheter carrying a balloon 42 is advanced over the guidewire 40 into a blood vessel 7 in a location containing an obstruction formed by plaque. The balloon 42 can then inflated at the desired location to compress the plaque and widen the vessel 7 (FIG. 7). The balloon 42 can then be deflated and removed.

Figure 8:
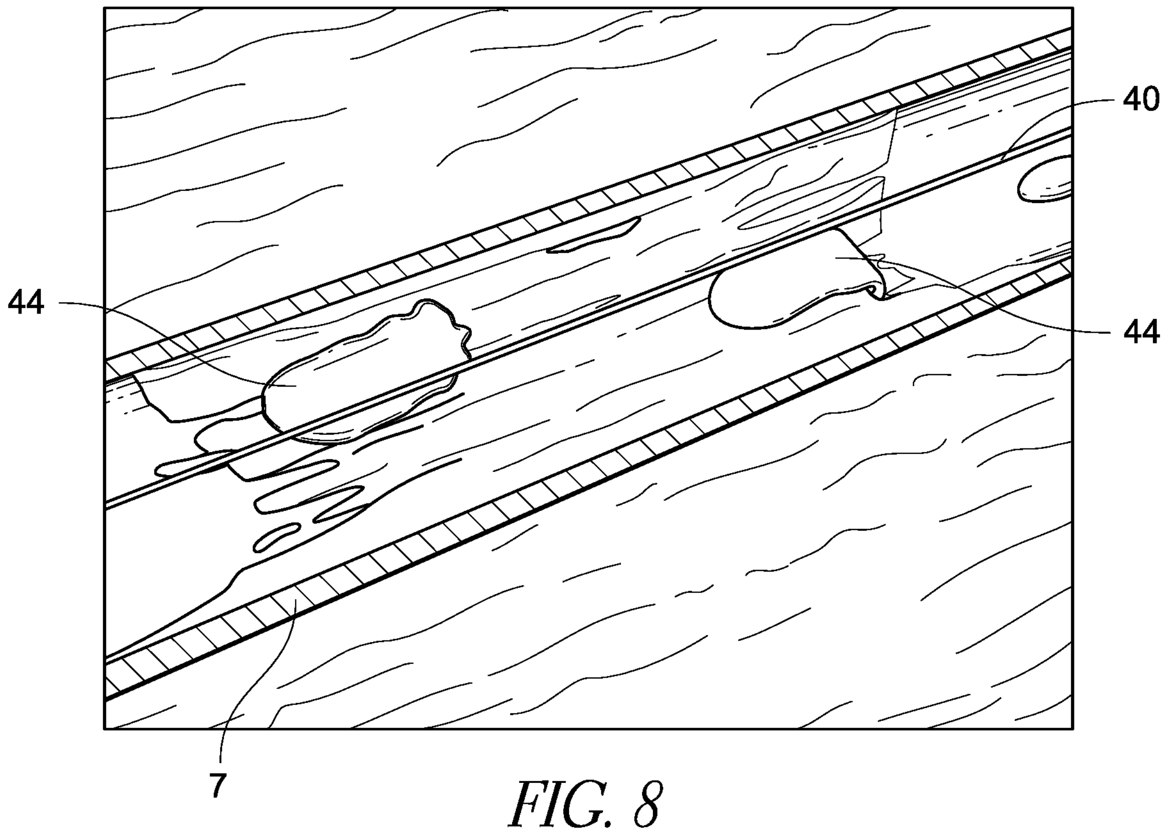

While widening the vessel 7, a dissection 44 of the plaque may be caused by the angioplasty (FIG. 8). An angiogram can be performed after the angioplasty to visualize the vessel where the angioplasty was performed and determine if there is evidence of post-angioplasty dissection or surface irregularity. An implant 10 according to disclosure herein can then be used to secure the plaque dissection 44 or other surface irregularity (for example, a remaining stenosis or narrowed portion of the vessel) to the lumen wall 7 where needed. As noted above, the implant 10 can be particularly useful where loose plaque is found at calcified lesions.

Figure 9:
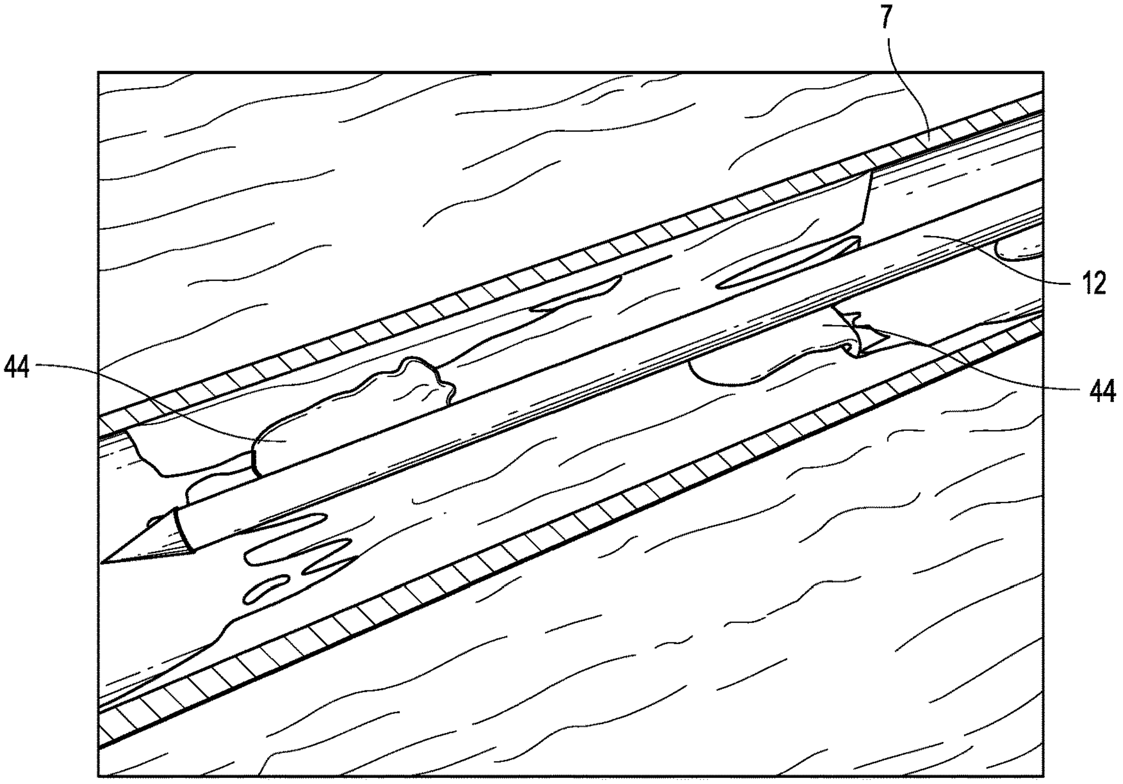
Figure 10:
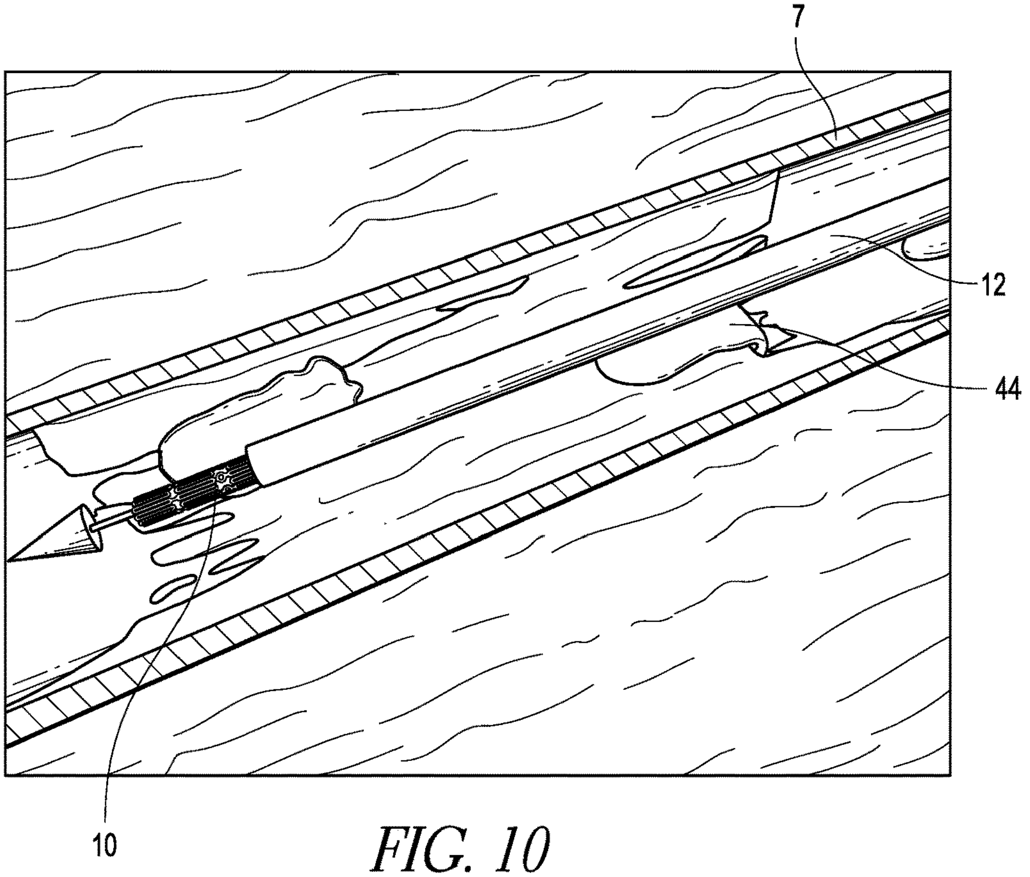
Figure 11:
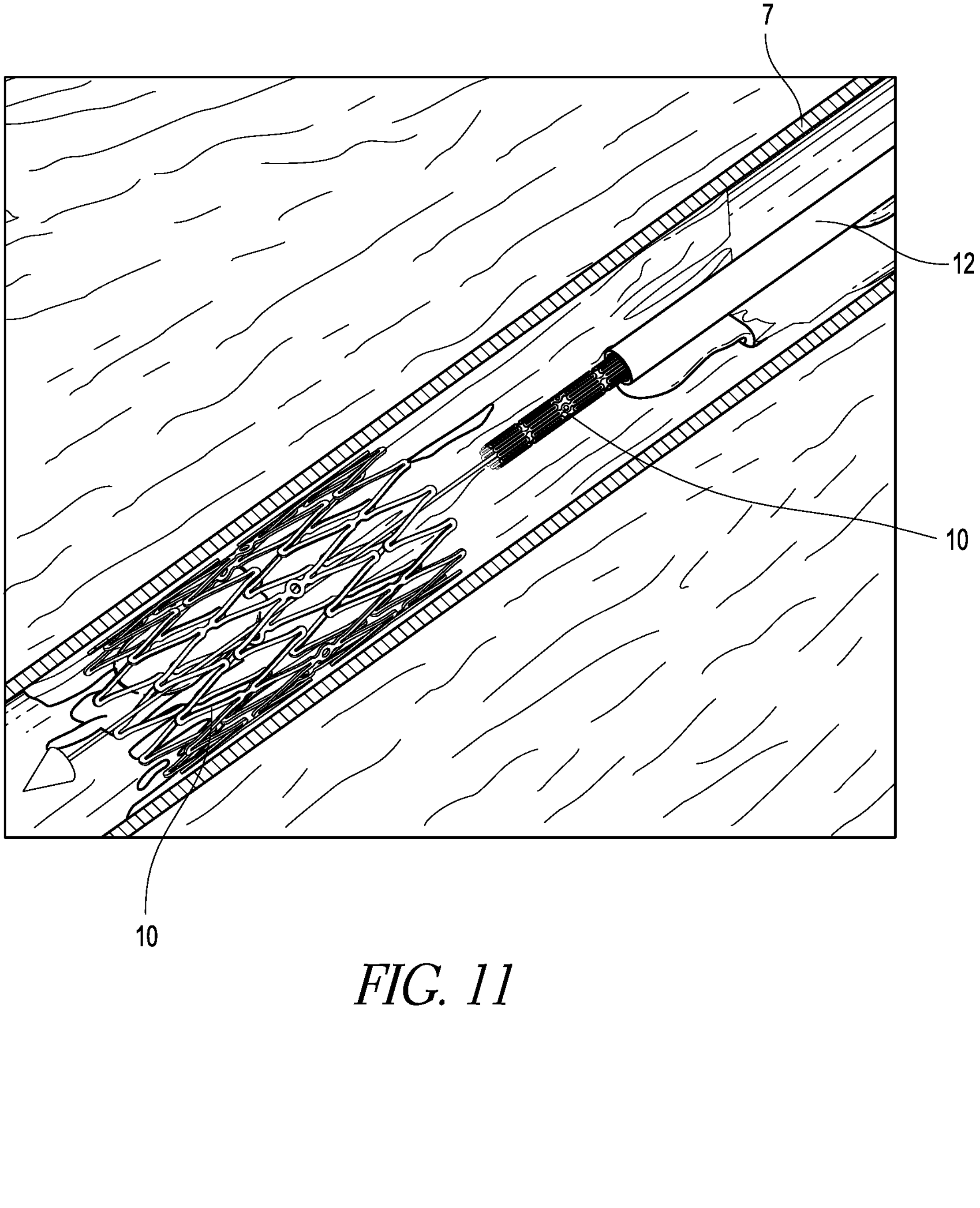

The delivery catheter 1 preloaded with one or more implants 10 according to one or more of the embodiments described herein can be advanced through the vessel 7 and along the guidewire 40 to the treatment site (FIG. 9). In some embodiments, a new or separate guidewire and cannula can be used. A distal most marker, either on the catheter or on the distal most implant 10, can be positioned under visualization at the treatment location. An outer sheath 12 can be withdrawn, exposing a portion of the implant 10. As has been discussed, the outer sheath 12 can be withdrawn until a set point and then the position of the catheter within the vessel can be adjusted, if necessary, to ensure precise placement of the implant 10 (FIG. 9). The set point can be for example, right before uncovering any of the implants, uncovering a portion or all of a ring, uncovering a ring etc.

The implant 10 can then be released in the desired location in the vessel lumen. As discussed previously, simultaneous placement can result upon release of some embodiments of the implant 10. Additional implants 10 can then be placed as desired (FIG. 10) in a distal to proximal placement within the treatment segment of the vessel.

In some embodiments, the precise placement of the implants 10 can be set upon positioning of the catheter within the vessel based on the position of a marker on the catheter and/or the implant 10. Once positioned, one or more implants can then be deployed while maintaining the catheter in place and slowly retracting the sheath.

Upon placement of the second implant 10 an intravascular construct is formed in situ. The in situ placement can be in any suitable vessel, such as in any peripheral artery. The construct need not be limited to just two implants 10. A plurality of at least three, four, five, six or more intravascular implants 10 (or any of the other implants herein) can be provided in an intravascular construct formed in situ. In one embodiment each of the plurality of implants has a length of no more than about 14 mm. In one configuration, at least one of, e.g., each of, the implants are spaced apart from an adjacent implant by at least about 4 mm, or between about 4 mm and 8 mm or between about 6 mm and 14 mm. Although certain embodiments have a length of 12 mm or less, other embodiments can be longer, e.g., up to about 15 mm long. Also, neighboring implants 10 can be positioned as close as 4 mm apart, particularly in vessels that are less prone to bending or other movements. In the various delivery catheters described herein, the spacing between implanted implants can be controlled to maintain a set or a minimum distance between each implant. As can be seen, the delivery catheters and/or implants can include features that help maintain the desired distance between implants. Maintaining proper inter-implant spacing can help ensure that the implants are distributed over a desired length without contacting each other or bunching up in a certain region of the treated vessel. This can help to prevent kinking of the vessel in which they are disposed.

While a one, two, or three implant construct formed in situ may be suitable for certain indications, an intravascular construct having at least 4, 5, or at least 6 intravascular implants may be advantageous for treating loose plaque, vessel flaps, dissections or other maladies that are significantly longer. For example, while most dissections are focal (e.g., axially short), a series of dissections may be considered and treated as a more elongated malady.

Figure 12:
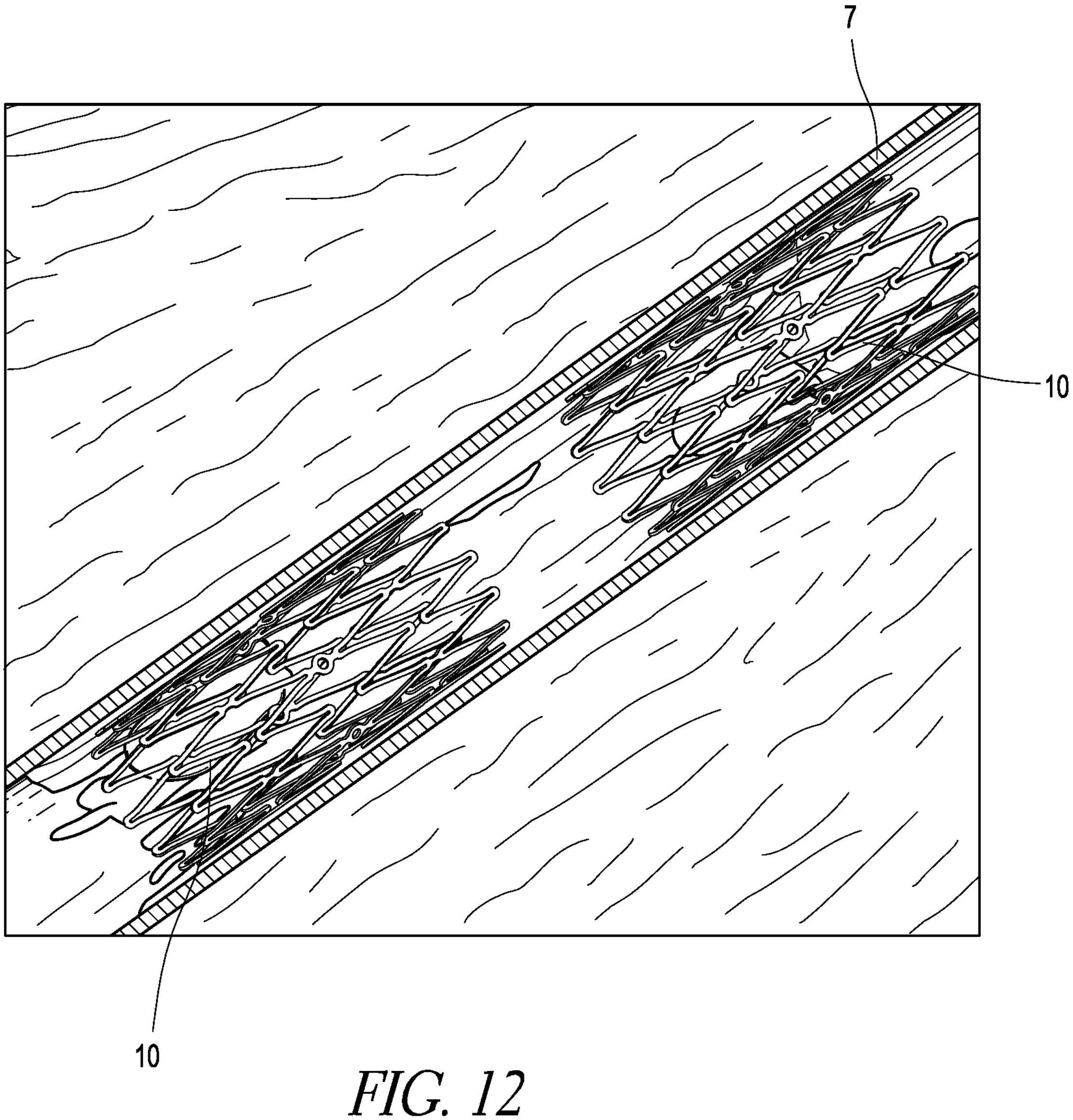

Optionally, once the implants 10 are in place, the angioplasty balloon can be returned to the treatment site and inflated to expand the implants 10 to the desired state of expansion. FIG. 12 shows the plaque implants 10 in their final implanted state.

As described above, more than one intravascular implant 10 can be accurately deployed in positions along the length of a plaque accumulation site where specific outward expansion forces are needed to stabilize the site and/or hold a dissection and/or pieces of loose plaque out of the way of blood flow and/or to expand portions of the site where the vessel remain narrowed. By using a series of implants, over-scaffolding of the vessel can be avoided. A reduction in cellular response is believed to be achieved partly through a reduction of surface area contact between the implant 10 and the blood vessel lumen as compared to using a single stent across the same treatment area.

In several embodiments, one purpose of the implants described herein, as distinct from traditional stenting, is to reduce the amount of implanted foreign material to a minimum while still performing focal treatment of the blood vessel condition so as to cause a minimum of blood vessel wall reaction and adverse post-treatment restenosis. The implant 10 can be designed to have substantially less metal coverage and/or contact with the blood vessel surface, thereby inciting less acute and chronic inflammation. Reduced contact area of implanted material against the blood vessel wall is correlated with a lower incidence of intimal hyperplasia and better long-term patency. Substantially reduced length along the axial distance of the blood vessel permits a more targeted treatment, correlates with less foreign body coverage of the blood vessel surface, avoids covering portions of the surface that are not in need of coverage, and correlates with both early and late improved patency of blood vessel reconstructions.

The implant 10 can be deployed only where needed to tack down plaque that has been disrupted by balloon angioplasty or other mechanisms and/or or to expand portions of the vessel that are subjected to residual stenosis after balloon dilations, for example, in more calcified lesions. Advantageously, in several embodiments, rather than cover an entire area of treatment, more than one implant 10 can be placed locally without overlap and selectively, for example, not extending into normal or less diseased artery segments. This permits the blood vessel to retain its natural flexibility because there is minimal to no scaffolding when a small profile implant is used locally or even when multiple implants are spaced apart over the length of treatment.

While the methods and devices described herein may be susceptible to various modifications and alternative forms, specific examples thereof have been shown in the drawings and are described in detail herein. It should be understood, however, that the inventive subject matter is not to be limited to the particular forms or methods disclosed, but, to the contrary, covers all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages. The methods disclosed herein may include certain actions taken by a practitioner; however, the methods can also include any third-party instruction of those actions, either expressly or by implication. For example, actions such as "deploying a self-expanding implant" include "instructing deployment of a self-expanding implant." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 7 mm" includes "7 mm" and numbers and ranges preceded by a term such as "about" or "approximately" should be interpreted as disclosing numbers and ranges with or without such a term such that this application supports claiming the number and ranges disclosed in the specification and/or claims with or without the term such as "about" or "approximately" before such numbers or ranges. Phrases preceded by a term such as "substantially" include the recited phrase and should be interpreted based on the circumstances (e.g., as much as reasonably possible under the circumstances). For example, "substantially straight" includes "straight."

What is claimed is:

1. An intravascular implant comprising:

a pair of inner rings comprising a distal inner ring and a proximal inner ring, the distal and proximal inner rings each being formed by a plurality of struts connected by apices to form a zig-zag pattern;

a plurality of inner bridges that extend between every other opposing adjacent apices of the distal and proximal inner rings; each of the plurality of inner bridges forming an eyelet;

a pair of outer rings comprising a distal outer ring and a proximal outer ring; the distal and proximal outer rings each being formed by a plurality of struts connected by apices to form a zig-zag pattern; and a plurality of outer bridge members, the plurality of outer bridge members including outer bridge members that extend between opposing adjacent inward apices of the distal outer ring and outward apices of the distal inner ring and the plurality of outer bridge members including outer bridge members that extend between opposing adjacent inward apices of the proximal outer ring and outward apices of the proximal inner ring; wherein the plurality of outer bridges connects every other opposing adjacent apices of the distal outer ring and distal inner ring and wherein the plurality of outer bridges connects every other opposing adjacent apices of the proximal outer ring and proximal inner ring.

2. The intravascular implant of claim 1, wherein the eyelet on each of the plurality of inner bridges is circular.

3. The intravascular implant of claim 1, wherein the plurality of inner bridges are located longitudinally between the plurality of outer bridges.

4. The intravascular implant of claim 3, wherein the plurality of outer bridges are linear.

5. The intravascular implant of claim 1, wherein the implant comprises Nitinol or is made of Nitinol.

6. The intravascular implant of claim 1, wherein the eyelet includes a radiopaque marker.

7. The intravascular implant of claim 1, wherein the implant exhibits a change of radial expansion or compression force of less than 0.3 N/mm over at least a 4 mm outer diameter expansion range.

8. The intravascular implant of claim 1, wherein the implant has an expanded diameter that is greater than 7 mm.

9. The intravascular implant of claim 1, wherein the implant has an expanded diameter range of at least 4 mm to 8 mm.

10. The intravascular implant of claim 9, wherein within the expanded diameter range the implant exhibits a change in both the radial expansion and compression force of less than 0.35 Newton per length of the implant along the implant's longitudinal axis (N/mm).

11. The intravascular implant of claim 9, wherein within the expanded diameter range the implant exhibits a change in both the radial expansion and compression force of between 0.35 and 0.1 Newton per length of the implant along the implant's longitudinal axis (N/mm).

12. The intravascular implant of claim 9, wherein within the expanded diameter range the implant exhibits a change in both the radial expansion and compression force of less than 3.5 Newtons.

13. The intravascular implant of claim 9, wherein within the expanded diameter range the implant exhibits a change in both the radial expansion and compression force of between 3.5 and 1 Newton.

14. The intravascular implant of claim 1, wherein the implant is self-expandable.

15. The intravascular implant of claim 1, wherein the pair of inner rings, the plurality of inner bridges, the pair of outer rings and the plurality of outer bridge members form cells and wherein there are between 1 and 5 columns of cells.

16. The intravascular implant of claim 1, wherein the pair of inner rings, the plurality of inner bridges, the pair of outer rings and the plurality of outer bridge members form cells, and wherein there are only three columns of cells.

17. The intravascular implant of claim 1, wherein the implant exhibits an expansion force during an expanded diameter range of at least 4 mm to 8 mm of between 0.7 and 0.18 Newton per length of the implant along the implant's longitudinal axis (N/mm).

18. The intravascular implant of claim 1, wherein the implant exhibits an expansion force during an expanded diameter range of at least 4 mm to 8 mm of between 7 and 2 Newtons.

19. The intravascular implant of claim 1, wherein the implant exhibits a compression force during an expanded diameter range of at least 4 mm to 8 mm of between 0.4 and 1.25 Newtons per length of the implant along the implant's longitudinal axis (N/mm).

20. The intravascular implant of claim 1, wherein the implant exhibits a compression force during an expanded diameter range of at least 4 mm to 8 mm of between 4 Newtons and 13 Newtons.

* * * * *